(12) United States Patent
Conn et al.

(10) Patent No.: US 10,399,948 B2
(45) Date of Patent: Sep. 3, 2019

(54) NEGATIVE ALLOSTERIC MODULATORS OF METABOTROPIC GLUTAMATE RECEPTOR 3

(71) Applicant: Vanderbilt University, Nashville, TN (US)

(72) Inventors: P. Jeffrey Conn, Nashville, TN (US); Craig W. Lindsley, Brentwood, NC (US); Kyle A. Emmitte, Aledo, TX (US); Julie L. Engers, Brentwood, TN (US); Katrina A. Bollinger, Murfreesboro, TN (US); Megan M. Breiner, Memphis, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/549,944

(22) PCT Filed: Feb. 10, 2016

(86) PCT No.: PCT/US2016/017318
§ 371 (c)(1),
(2) Date: Aug. 9, 2017

(87) PCT Pub. No.: WO2016/130652
PCT Pub. Date: Aug. 18, 2016

(65) Prior Publication Data
US 2018/0022712 A1 Jan. 25, 2018

Related U.S. Application Data

(60) Provisional application No. 62/114,484, filed on Feb. 10, 2015.

(51) Int. Cl.
| | |
|---|---|
| *C07D 213/04* | (2006.01) |
| *C07D 213/69* | (2006.01) |
| *C07D 401/04* | (2006.01) |
| *C07D 401/12* | (2006.01) |
| *A61K 31/444* | (2006.01) |
| *A61K 31/435* | (2006.01) |
| *C07D 239/60* | (2006.01) |
| *C07D 237/16* | (2006.01) |
| *C07D 239/52* | (2006.01) |

(52) U.S. Cl.
CPC ......... *C07D 239/60* (2013.01); *C07D 213/04* (2013.01); *C07D 213/69* (2013.01); *C07D 237/16* (2013.01); *C07D 239/52* (2013.01); *C07D 401/04* (2013.01); *C07D 401/12* (2013.01)

(58) Field of Classification Search
None
See application file for complete search history.

(56) References Cited

U.S. PATENT DOCUMENTS

| | | | |
|---|---|---|---|
| 2004/0142932 A1* | 7/2004 | Hepperle | C07D 237/16 514/247 |
| 2005/0176775 A1 | 8/2005 | Devadas et al. | |
| 2009/0264426 A1 | 10/2009 | Sakuraba et al. | |
| 2012/0058940 A9 | 3/2012 | Guzzo et al. | |
| 2012/0172391 A1 | 7/2012 | Conn et al. | |
| 2012/0258959 A1 | 10/2012 | Wacker et al. | |
| 2014/0315903 A1 | 10/2014 | Imogai et al. | |

FOREIGN PATENT DOCUMENTS

| | | |
|---|---|---|
| WO | 2006048152 | 5/2006 |
| WO | 2013105676 | 7/2013 |

OTHER PUBLICATIONS

Database Registry Chemical Abstracts Service, Columbus, Ohio, Accession No. RN 113516-63-5, Entered STN: Mar. 26, 1988.*
Haga, Y. Discovery of novel phenylpyridone derivatives as potent and selective MCH1R antagonists. Bioorganic & Medicinal Chemistry. 19 (2011) 883-893.*
PCT/US2016/17318 International Search Report and Written Opinion of the International Searching Authority dated Apr. 8, 2016 (9 pages).

\* cited by examiner

*Primary Examiner* — Samantha L Shterengarts
(74) *Attorney, Agent, or Firm* — Michael Best & Friedrich LLP

(57) ABSTRACT

Described are negative allosteric modulators of metabotropic glutamate receptor 3 (mGlu3), pharmaceutical compositions including the compounds, and methods of using the compounds and compositions for treating depression, cognitive disorders, schizophrenia, Alzheimer's disease, or cancer in a subject.

11 Claims, No Drawings

NEGATIVE ALLOSTERIC MODULATORS OF METABOTROPIC GLUTAMATE RECEPTOR 3

CROSS-REFERENCE TO RELATED APPLICATIONS

This application is a national stage filing under 35 U.S.C. § of International Patent Application No. PCT/US2016/017318, which claims priority to U.S. Provisional Application No. 62/114,484, filed Feb. 10, 2015, the entire contents of which are incorporated herein by reference.

STATEMENT OF GOVERNMENT INTEREST

This invention was made with government support under Grant number 1 R01 MH99269-01 awarded by the National Institute of Mental Health (NIMH). The government has certain rights in the invention.

TECHNICAL FIELD

The present disclosure relates to compounds, compositions, and methods for treating metabotropic glutamate receptor 3 related diseases and/or disorders, such as depression, cognitive disorders, schizophrenia, Alzheimer's disease, and cancer.

BACKGROUND

Metabotropic glutamate receptors (mGlus), a class of G-protein coupled receptor (GPCR) family C, have recently emerged as targets of potential therapeutic value. They bind glutamate, an amino acid that is the most prominent excitatory neurotransmitter in the human central nervous system (CNS). mGlus are known to activate biochemical cascades, leading to the modification of other proteins. For example, this can lead to changes in a synapse's excitability by presynaptic inhibition of neurotransmission, or modulation and even induction of postsynaptic responses.

Metabotropic glutamate receptor 3 ($mGlu_3$) is one of eight mGlus that have been identified, and, along with $mGlu_2$, is classified as a group II mGlu. Group II mGlus play an important role is synaptic plasticity, which directly effects cognitive function (including learning and memory), among other things. The effects of group II mGlus occur primarily presynaptically via their inhibition of glutamate release. These effects can also be due to the inhibition of non-vesicular glutamate release from glia. However, group II receptors are known to also reduce the activity of postsynaptic potentials, both excitatory and inhibitory, in the cortex. It is also suggested that $mGlu_3$ is involved with regulating non-synaptic glutamate since it is localized away from active synaptic zones.

Dysfunction of $mGlu_3$ has been implicated in many diseases and/or disorders. Hence, targeting $mGlu_3$ activity has been the subject of much investigation. Several reports have highlighted its link to a variety of diseases, such as cognitive disorders, schizophrenia, depression, Alzheimer's disease, and cancer. Accordingly, there exists a need for modulators of $mGlu_3$.

SUMMARY OF THE INVENTION

In one aspect, disclosed are compounds of formula (I),

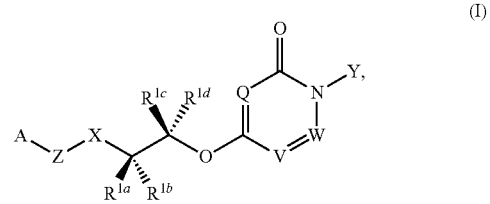

or pharmaceutically acceptable salts thereof, wherein
A is aryl, heteroaryl, heterocycle, or cycloalkyl;
Z is a bond, O, S, $NR^2$, or $CR^{1g}R^{1h}$;
X is $-(CR^{1e}R^{1f})_m-$, O, S, $NR^2$, $-C(O)-$, $-O-C(O)-$, $-C(O)-O-$, $-O-C(O)-NR^2-$, $-C(O)-NR^2-$, $-NR^2-C(O)-$, $-NR^2-C(O)-O-$, $-NR^2-C(O)-NR^2-$, $-NR^2-SO_2-$, $-SO-$, or $-SO_2-$;
$R^{1e}$, $R^{1f}$, $R^{1g}$ and $R^{1h}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy;
m is 1-3;
$R^2$ is hydrogen, $C_1$-$C_3$ alkyl or $C_1$-$C_3$ haloalkyl;
$R^{1a}$, $R^{1b}$, $R^{1c}$, and $R^{1d}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy;
Q is N or $CR^{3a}$;
V is N or $CR^{3b}$;
W is N or $CR^{3c}$; wherein no more than one of Q, V and W is N;
$R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and
Y is aryl, heteroaryl, cycloalkyl, or heterocycle; wherein said aryl, heteroaryl, cycloalkyl, and heterocycle, at each occurrence, are independently substituted or unsubstituted.

Also disclosed are pharmaceutical compositions comprising the compounds, methods of making the compounds, and methods of using the compounds for treatment of metabotropic glutamate receptor 3 related diseases and/or disorders.

DETAILED DESCRIPTION

Disclosed herein are negative allosteric modulators (NAMs) of $mGlu_3$. The modulators can be compounds of formula (I). Compounds of formula (I) exhibit selectivity for $mGlu_3$ over other mGlu receptors, and in particular, $mGlu_2$. Compounds of formula (I) can also exhibit selectivity for $mGlu_3$ over mGlus. Compounds of formula (I) can be used to treat or prevent diseases and disorders associated with $mGlu_3$ by modulating $mGlu_3$ activity. $mGlu_3$ has been implicated in a number of different diseases and disorders including, but not limited to, depression, cognitive disorders, schizophrenia, Alzheimer's disease, and cancer, such as glioma.

Since the orthosteric binding sites of the mGlu isoforms are highly conserved, very few selective modulators of the mGlus that bind at the orthosteric site have been identified. One strategy to selectively bind and modulate the mGlus includes identifying allosteric sites which may be amenable to modulation by a small molecule. In particular, negative allosteric modulation of $mGlu_3$ can result in inhibition of processes governed by mGlu$_3$ and provide therapeutic benefits for disorders caused by mGlu$_3$ dysfunction.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkoxyalkyl" as used herein, refers to an alkoxy group, as defined herein, appended to the parent molecular moiety through an alkyl group, as defined herein.

The term "alkoxyfluoroalkyl" as used herein, refers to an alkoxy group, as defined herein, appended to the parent molecular moiety through a fluoroalkyl group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "aryl" as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl.

The term "cyanoalkyl" as used herein, means at least one —CN group, is appended to the parent molecular moiety through an alkylene group, as defined herein.

The term "cyanofluoroalkyl" as used herein, means at least one —CN group, is appended to the parent molecular moiety through a fluoroalkyl group, as defined herein.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "halocycloalkyl" as used herein, means a cycloalkyl group, as defined herein, in which one or more hydrogen atoms are replaced by a halogen.

The term "heteroalkyl" as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, thiazolyl, and quinolinyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3] heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy" as used herein, means an —OH group.

The term "hydroxyalkyl" as used herein, means at least one —OH group, is appended to the parent molecular moiety through an alkylene group, as defined herein.

The term "hydroxyfluoroalkyl" as used herein, means at least one —OH group, is appended to the parent molecular moiety through a fluoroalkyl group, as defined herein.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

In one aspect, disclosed is a compound of formula (I):

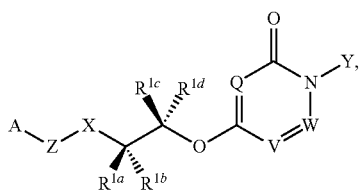

or a pharmaceutically acceptable salt thereof, A is aryl, heteroaryl, heterocycle, or cycloalkyl; Z is a bond, O, S, NR$^2$, or CR$^{1g}$R$^{1h}$; X is —(CR$^{1e}$R$^{1f}$)$_m$—, O, S, NR$^2$, —C(O)—, —O—C(O)—, —C(O)—O—, —O—C(O)—NR$^2$—, —C(O)—NR$^2$—, —NR$^2$—C(O)—, —NR$^2$—C(O)—O—, —NR$^2$—C(O)—NR$^2$—, —NR$^2$—SO$_2$—, —SO—, or —SO$_2$—; R$^{1e}$, R$^{1f}$, R$^{1g}$ and R$^{1h}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; m is 1-3; R$^2$ is hydrogen, C$_1$-C$_3$ alkyl or C$_1$-C$_3$ haloalkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^{3c}$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl, heteroaryl, heterocycle, or cycloalkyl; Z is a bond, O, S, NR$^2$, or CR$^{1g}$R$^{1h}$; X is —(CR$^{1e}$R$^{1f}$)$_m$—, O, S, NR$^2$, —C(O)—, —O—C(O)—, —C(O)—O—, —O—C(O)—NR$^2$—, —C(O)—NR$^2$—, —NR$^2$—C(O)—, —NR$^2$—C(O)—O—, —NR$^2$—C(O)—NR$^2$—, —NR$^2$—SO$_2$—, —SO—, or —SO$_2$—; R$^{1e}$, R$^{1f}$, R$^{1g}$ and R$^{1h}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; m is 1-3; R$^2$ is hydrogen, C$_1$-C$_3$ alkyl or C$_1$-C$_3$ haloalkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^{3c}$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, A is aryl or heteroaryl.

In certain embodiments, A is aryl or heteroaryl, with 0-3 substituents independently selected from halogen, cyano, C$_1$-C$_6$ alkyl, C$_1$-C$_6$ fluoroalkyl, C$_1$-C$_6$ alkoxy(C$_1$-C$_6$)alkyl, C$_1$-C$_6$ hydroxyalkyl, C$_1$-C$_6$ hydroxy(C$_1$-C$_6$)fluoroalkyl, C$_1$-C$_6$ alkoxy(C$_1$-C$_6$)fluoroalkyl, C$_1$-C$_6$ cyanoalkyl, C$_1$-C$_6$ cyanofluoroalkyl, C$_3$-C$_8$ cycloalkyl, C$_3$-C$_8$ fluorocycloalkyl, OR$^4$, and NR$^{5a}$R$^{5b}$; wherein R$^4$ is hydrogen, C$_1$-C$_6$ alkyl or C$_1$-C$_6$ fluoroalkyl; wherein R$^{5a}$ and R$^{5b}$ are each independently hydrogen, C$_1$-C$_6$ alkyl, C$_3$-C$_8$ cycloalkyl, or C$_1$-C$_6$ heteroalkyl; or R$^{5a}$ and R$^{5b}$ together with the nitrogen atom to which they are attached form a heterocycle; wherein each R$^{5a}$ and R$^{5b}$ are substituted with 0-3 fluorine atoms.

In certain embodiments, A is aryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$)alkyl, and OR$^4$; wherein R$^4$ is hydrogen, C$_1$-C$_3$ alkyl, or C$_1$-C$_3$ fluoroalkyl.

In certain embodiments, A is heteroaryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$)alkyl, and OR$^4$; wherein R$^4$ is hydrogen, C$_1$-C$_3$ alkyl, or C$_1$-C$_3$ fluoroalkyl.

In certain embodiments, A is phenyl substituted with 0-2 substituents independently selected from fluoro, chloro, methoxyethyl, and cyano.

In certain embodiments, A is pyridyl substituted with 0-2 substituents independently selected from fluoro, chloro, methoxyethyl, and cyano.

In certain embodiments, A is a monocyclic heteroaryl. In certain embodiments, A is a monocyclic heterocycle. In certain embodiments, A is bicyclic heterocycle. In certain embodiments, A is a monocyclic heterocycle fused to a phenyl group. In certain embodiments, A is a monocyclic heterocycle fused to a monocyclic cycloalkenyl. In certain embodiments, A is a monocyclic heterocycle fused to a monocyclic heterocycle. In certain embodiments, A is a spiro heterocycle. In certain embodiments, A is a bridged monocyclic heterocycle ring system. In certain embodiments, A is a tricyclic heterocycle. In certain embodiments, A is a bicyclic heterocycle fused to a phenyl group. In certain embodiments, A is a bicyclic heterocycle fused to a monocyclic cycloalkyl. In certain embodiments, A is a bicyclic heterocycle fused to a monocyclic cycloalkenyl. In certain embodiments, A is a bicyclic heterocycle fused to a monocyclic heterocycle. In certain embodiments, A is a bicyclic heterocycle in which two non-adjacent atoms of the bicyclic ring are linked by an alkylene bridge. In certain embodiments, A is an aromatic monocyclic ring. In certain embodiments, A is an aromatic bicyclic ring system. In certain embodiments, A is a cycloalkyl. In certain embodiments, A is unsubstituted. In certain embodiments, A is substituted with 1, 2, 3, 4, 5, 6, or 7 functional groups independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, fonylamino, sulfinylamino, sulfonyl, alkylsulfonyl, arylsulfonyl, aminosulfonyl, sulfinyl, —COOH, ketone, amide, carbaminate, and acyl.

In certain embodiments, A is phenyl. In certain embodiments, A is pyridyl. In certain embodiments, A is isothiazolyl. In certain embodiments, A is thiazolyl. In certain embodiments, A is pyrazolyl. In certain embodiments, A is imidazolyl. In certain embodiments, A is pyrrolyl. In certain embodiments, A is thienyl. In certain embodiments, A is furanyl. In certain embodiments, A is benzofuranyl. In certain embodiments, A is benzothienyl. In certain embodiments, A is indolyl. In certain embodiments, A is naphthyl. In certain embodiments, A is quinolinyl. In certain embodiments, A is tetrahydroquinolinyl. In certain embodiments, A is pyrimidinyl. In certain embodiments, A is pyridazinyl. In certain embodiments, A is pyrazinyl. In certain embodiments, A is oxazolyl. In certain embodiments, A is isoxazolyl.

In certain embodiments, Z is a bond.

In certain embodiments, X is —$(CR^{1e}R^{1f})_m$—, O, S, $NR^2$, —SO—, or —$SO_2$—; wherein $R^{1e}$ and $R^{1f}$ are independently hydrogen, fluoro, or $C_1$-$C_3$ alkyl; and $R^2$ is hydrogen, $C_1$-$C_3$ alkyl or $C_1$-$C_3$ fluoroalkyl.

In certain embodiments, X is O, S, or $NR^2$; wherein $R^2$ is hydrogen, $C_1$-$C_3$ alkyl or $C_1$-$C_3$ fluoroalkyl.

In certain embodiments, Z is a bond, O, S, $NR^2$, or $CR^{1g}R^{1h}$; and X is —$(CR^{1e}R^{1f})_m$—, O, S, $NR^2$, —C(O)—, —O—C(O)—, —C(O)—O—, —O—C(O)—$NR^2$—, —C(O)—$NR^2$—, —$NR^2$—C(O)—, —$NR^2$—C(O)—O—, —$NR^2$—C(O)—$NR^2$—, —$NR^2$—$SO_2$—, —SO—, or —$SO_2$—; provided that that Z and X do not form an O—O or an N—N bond.

In certain embodiments, $R^{1a}$, $R^{1b}$, $R^{1c}$, and $R^{1d}$ are each independently hydrogen, fluoro, $C_1$-$C_3$ alkyl, or $C_1$-$C_3$ fluoroalkyl.

In certain embodiments, $R^{1a}$, $R^{1b}$, $R^{1c}$, and $R^{1d}$ are each independently hydrogen or $C_1$-$C_3$ alkyl.

In certain embodiments, Q is $CR^{3a}$. In certain embodiments, Q is N.

In certain embodiments, V is $CR^{3b}$. In certain embodiments, V is N.

In certain embodiments, W is $CR^{3c}$. In certain embodiments, W is N.

In certain embodiments, Q is $CR^{3a}$; V is $CR^{3b}$; and W is $CR^{3c}$. In certain embodiments, Q is $CR^{3a}$; V is $CR^{3b}$; and W is $CR^{3c}$; wherein $R^{3a}$, $R^{3b}$, and $R^{3c}$ are hydrogen, halogen, or $C_1$-$C_3$ alkyl.

In certain embodiments, Q is N; V is $CR^{3b}$; and W is $CR^{3c}$. In certain embodiments, Q is N; V is $CR^{3b}$; and W is $CR^{3c}$; wherein $R^{3b}$ and $R^c$ are hydrogen, halogen, or $C_1$-$C_4$ alkyl.

In certain embodiments, Q is $CR^{3a}$; V is $CR^{3b}$; and W is N. In certain embodiments, Q is $CR^{3a}$; V is $CR^{3b}$; and W is N; wherein $R^{3a}$ and $R^{3b}$ are hydrogen, halogen, or $C_1$-$C_4$ alkyl.

In certain embodiments, $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy. In certain embodiments, $R^{3a}$, $R^{3b}$, and $R^{3c}$ are hydrogen, halogen, or $C_1$-$C_3$ alkyl. In certain embodiments, $R^{3a}$, $R^{3b}$, and $R^{3c}$ are hydrogen, fluoro, or $C_1$-$C_3$ alkyl.

In certain embodiments, Y is aryl, heteroaryl, cycloalkyl, or heterocycle. In certain embodiments, Y is aryl or heteroaryl.

In certain embodiments, Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl.

In certain embodiments, Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl.

In certain embodiments, Y is phenyl substituted with 0-2 substituents independently selected from fluoro and cyano. In certain embodiments, Y is pyridyl substituted with 0-2 substituents independently selected from fluoro and cyano.

In certain embodiments, Y is a monocyclic heteroaryl. In certain embodiments, Y is a monocyclic heterocycle. In certain embodiments, Y is bicyclic heterocycle. In certain embodiments, Y is a monocyclic heterocycle fused to a phenyl group. In certain embodiments, Y is a monocyclic heterocycle fused to a monocyclic cycloalkenyl. In certain embodiments, Y is a monocyclic heterocycle fused to a monocyclic heterocycle. In certain embodiments, Y is a spiro heterocycle. In certain embodiments, Y is a bridged monocyclic heterocycle ring system. In certain embodiments, Y is a tricyclic heterocycle. In certain embodiments, Y is a bicyclic heterocycle fused to a phenyl group. In certain embodiments, Y is a bicyclic heterocycle fused to a monocyclic cycloalkyl. In certain embodiments, Y is a bicyclic heterocycle fused to a monocyclic cycloalkenyl. In certain embodiments, Y is a bicyclic heterocycle fused to a monocyclic heterocycle. In certain embodiments, Y is a bicyclic heterocycle in which two non-adjacent atoms of the bicyclic ring are linked by an alkylene bridge. In certain embodiments, Y is an aromatic monocyclic ring. In certain embodiments, Y is an aromatic bicyclic ring system. In certain embodiments, Y is a cycloalkyl. In certain embodiments, Y is unsubstituted. In certain embodiments, Y is substituted with 1, 2, 3, 4, 5, 6, or 7 functional groups independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, Y is phenyl. In certain embodiments, Y is pyridyl. In certain embodiments, Y is isothiazolyl. In certain embodiments, Y is thiazolyl. In certain embodiments, Y is pyrazolyl. In certain embodiments, Y is imidazolyl. In certain embodiments, Y is pyrrolyl. In certain embodiments, Y is thienyl. In certain embodiments, Y is furanyl. In certain embodiments, Y is benzofuranyl. In certain embodiments, Y is benzothienyl. In certain embodiments, Y is indolyl. In certain embodiments, Y is naphthyl. In certain embodiments, Y is quinolinyl. In certain embodiments, Y is tetrahydroquinolinyl. In certain embodiments, Y is pyrimidinyl. In certain embodiments, Y is pyridazinyl. In certain embodiments, Y is pyrazinyl. In certain embodiments, Y is oxazolyl. In certain embodiments, Y is isoxazolyl.

In certain embodiments, A is aryl or heteroaryl; Z is a bond, O, S, $NR^2$, or $CR^{1g}R^{1h}$; X is —$(CR^{1e}R^{1f})_m$—, O, S, $NR^2$, —C(O)—, —O—C(O)—, —C(O)—O—, —O—C(O)—$NR^2$—, —C(O)—$NR^2$—, —$NR^2$C(O)—, —$NR^2$—C(O)—

O—, —NR$^2$—C(O)—NR$^2$—, —NR$^2$—SO$_2$—, —SO—, or —SO$_2$—; R$^{1e}$, R$^{1f}$, R$^{1g}$ and R$^{1h}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; m is 1-3; R$^2$ is hydrogen, C$_1$-C$_3$ alkyl or C$_1$-C$_3$ haloalkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^{3c}$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl with 0-3 substituents independently selected from halogen, cyano, C$_1$-C$_6$ alkyl, C$_1$-C$_6$ fluoroalkyl, C$_1$-C$_6$ alkoxy(C$_1$-C$_6$)alkyl, C$_1$-C$_6$ hydroxyalkyl, C$_1$-C$_6$ hydroxy(C$_1$-C$_6$)fluoroalkyl, C$_1$-C$_6$ alkoxy(C$_1$-C$_6$)fluoroalkyl, C$_1$-C$_6$ cyanoalkyl, C$_1$-C$_6$ cyanofluoroalkyl, C$_3$-C$_8$ cycloalkyl, C$_3$-C$_8$ fluorocycloalkyl, OR$^4$, and NR$^{5a}$R$^{5b}$; wherein R$^4$ is hydrogen, C$_1$-C$_6$ alkyl or C$_1$-C$_6$ fluoroalkyl; and R$^{5a}$ and R$^{5b}$ are each independently hydrogen, C$_1$-C$_6$ alkyl, C$_3$-C$_8$ cycloalkyl, or C$_1$-C$_6$ heteroalkyl; or R$^{5a}$ and R$^{5b}$ together with the nitrogen atom to which they are attached form a heterocycle; wherein each R$^{5a}$ and R$^{5b}$ are substituted with 0-3 fluorine atoms; Z is a bond, O, S, NR$^2$, or CR$^{1g}$R$^{1h}$; X is —(CR$^{1e}$R$^{1f}$)$_m$, O, S, NR$^2$, —C(O)—, —O—C(O)—, —C(O)—O—, —O—C(O)—NR$^2$—, —C(O)—NR$^2$—, —NR$^2$—C(O)—, —NR$^2$—C(O)—O—, —NR$^2$—C(O)—NR$^2$—, —NR$^2$—SO$_2$—, —SO—, or —SO$_2$—; R$^{1e}$, R$^{1f}$, R$^{1g}$ and R$^{1h}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; m is 1-3; R$^2$ is hydrogen, C$_1$-C$_3$ alkyl or C$_1$-C$_3$ haloalkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^3$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$) alkyl, and OR$^4$; wherein R$^4$ is hydrogen, C$_1$-C$_3$ alkyl, or C$_1$-C$_3$ fluoroalkyl; Z is a bond, O, S, NR$^2$, or CR$^{1g}$R$^{1h}$; X is —(CR$^{1e}$R$^{1f}$)$_m$—, O, S, NR$^2$, —C(O)—, —O—C(O)—, —C(O)—O—, —O—C(O)—NR$^2$—, —C(O)—NR$^2$—, —NR$^2$—C(O)—, —NR$^2$—C(O)—O—, —NR$^2$—C(O)—NR$^2$—, —NR$^2$—SO$_2$—, —SO—, or —SO$_2$—; R$^{1e}$, R$^{1f}$, R$^{1g}$ and R$^{1h}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; m is 1-3; R$^2$ is hydrogen, C$_1$-C$_3$ alkyl or C$_1$-C$_3$ haloalkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^3$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is heteroaryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$) alkyl, and OR$^4$; wherein R$^4$ is hydrogen, C$_1$-C$_3$ alkyl, or C$_1$-C$_3$ fluoroalkyl; Z is a bond, O, S, NR$^2$, or CR$^{1g}$R$^{1h}$; X is —(CR$^{1e}$R$^{1f}$)$_m$—, O, S, NR$^2$, —C(O)—, —O—C(O)—, —C(O)—O—, —O—C(O)—NR$^2$—, —C(O)—NR$^2$—, —NR$^2$—C(O)—, —NR$^2$—C(O)—O—, —NR$^2$—C(O)—NR$^2$—, —NR$^2$—SO$_2$—, —SO—, or —SO$_2$—; R$^{1e}$, R$^{1f}$, R$^{1g}$ and R$^{1h}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; m is 1-3; R$^2$ is hydrogen, C$_1$-C$_3$ alkyl or C$_1$-C$_3$ haloalkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^3$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is phenyl substituted with 0-2 substituents independently selected from fluoro, chloro, methoxyethyl, and cyano; Z is a bond, O, S, NR$^2$, or CR$^{1g}$R$^{1h}$; X is —(CR$^{1e}$R$^{1f}$)$_m$—, O, S, NR$^2$, —C(O)—, —O—C(O)—, —C(O)—O—, —O—C(O)—NR$^2$—, —C(O)—NR$^2$—, —NR$^2$—C(O)—, —NR$^2$—C(O)—O—, —NR$^2$—C(O)—NR$^2$—, —NR$^2$—SO$_2$—, —SO—, or —SO$_2$—; R$^{1e}$, R$^{1f}$, R$^{1g}$ and R$^{1h}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; m is 1-3; R$^2$ is hydrogen, C$_1$-C$_3$ alkyl or C$_1$-C$_3$ haloalkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^3$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is pyridyl substituted with 0-2 substituents independently selected from fluoro, chloro, methoxyethyl, and cyano; Z is a bond, O, S, NR$^2$, or CR$^{1g}$R$^{1h}$; X is —(CR$^{1e}$R$^{1f}$)$_m$—, O, S, NR$^2$, —C(O)—, —O—C(O)—, —C(O)—O—, —O—C(O)—NR$^2$—, —C(O)—NR$^2$—, —NR$^2$—C(O)—, —NR$^2$—C(O)—O—, —NR$^2$—C(O)—NR$^2$—, —NR$^2$—SO$_2$—, —SO—, or —SO$_2$—; R$^{1e}$, R$^{1f}$, R$^{1g}$ and R$^{1h}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; m is 1-3; R$^2$ is hydrogen, C$_1$-C$_3$ alkyl or C$_1$-C$_3$ haloalkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^3$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl, heteroaryl, heterocycle, or cycloalkyl; Z is a bond; X is —(CR$^{1e}$R$^{1f}$)$_m$, O, S, NR$^2$, —C(O)—, —O—C(O)—, —C(O)—O—, —O—C(O)—NR$^2$—, —C(O)—NR$^2$—, —NR$^2$—C(O)—, —NR$^2$—C(O)—O—, —NR$^2$—C(O)—NR$^2$—, —NR$^2$—SO$_2$—, —SO—, or —SO$_2$—; R$^{1e}$ and R$^{1f}$ are each independently hydrogen, halogen, C$_1$-C$_3$ alkyl, C$_1$-C$_3$ alkoxy, C$_1$-C$_3$ haloalkyl, or $C_1$-$C_3$ haloalkoxy; m is 1-3; $R^2$ is hydrogen, $C_1$-$C_3$ alkyl or $C_1$-$C_3$ haloalkyl; $R^{1a}$, $R^{1b}$, $R^{1c}$, and $R^d$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; Q is N or $CR^{3a}$; V is N or $CR^{3b}$; W is N or $CR^3$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl; Z is a bond; X is —(CR$^{1e}$R$^{1f}$)$_m$—, O, S, NR$^2$, —C(O)—, —O—C(O)—, —C(O)—O—, —O—C(O)—NR$^2$—, —C(O)—NR$^2$—, —NR—C(O)—, —NR$^2$—C(O)—O—, —NR$^2$—C(O)—NR$^2$—, —NR$^2$—SO$_2$—, —SO—, or —SO$_2$—; $R^{1e}$ and $R^{1f}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; m is 1-3; $R^2$ is hydrogen, $C_1$-$C_3$ alkyl or $C_1$-$C_3$ haloalkyl; $R^{1a}$, $R^{1b}$, $R^{1c}$, and $R^{1d}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; Q is N or $CR^{3a}$; V is N or $CR^{3b}$; W is N or $CR^{3c}$; wherein no more than one of Q, V and W is N; $R^{3a}$, $R^{3b}$ and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, OR$^4$, and NR$^{5a}$R$^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is —(CR$^{1e}$R$^{1f}$)$_m$—, O, S, NR$^2$, —C(O)—, —O—C(O)—, —C(O)—O—, —O—C(O)—NR$^2$—, —C(O)—NR$^2$—, —NR$^2$—C(O)—, —NR$^2$—C(O)—O—, —NR$^2$—C(O)—NR$^2$—, —NR$^2$—SO$_2$—, —SO—, or —SO$_2$—; $R^{1e}$ and $R^{1f}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; m is 1-3; $R^2$ is hydrogen, $C_1$-$C_3$ alkyl or $C_1$-$C_3$ haloalkyl; $R^{1a}$, $R^{1b}$, $R^{1c}$, and $R^{1d}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; Q is N or $CR^{3a}$; V is N or $CR^{3b}$; W is N or $CR^{3c}$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and OR$^4$; wherein $R^4$ is hydrogen, $C_1$-$C_3$ alkyl, or $C_1$-$C_3$ fluoroalkyl; Z is a bond; X is —(CR$^{1e}$R$^{1f}$)$_m$—, O, S, NR$^2$, —C(O)—, —O—C(O)—, —C(O)—O—, —O—C(O)—NR$^2$—, —C(O)—NR$^2$—, —NR$^2$—C(O)—, —NR$^2$—C(O)—O—, —NR$^2$—C(O)—NR$^2$—, —NR$^2$—SO$_2$—, —SO—, or —SO$_2$—; $R^{1e}$ and $R^{1f}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; m is 1-3; $R^2$ is hydrogen, $C_1$-$C_3$ alkyl or $C_1$-$C_3$ haloalkyl; $R^{1a}$, $R^{1b}$, $R^{1c}$, and $R^{1d}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; Q is N or $CR^{3a}$; V is N or $CR^{3b}$; W is N or $CR^3$; wherein no more than one of Q, V and W is N; $R^{3a}$, $R^{3b}$ and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and OR$^4$; wherein $R^4$ is hydrogen, $C_1$-$C_3$ alkyl, or $C_1$-$C_3$ fluoroalkyl; Z is a bond; X is —(CR$^{1e}$R$^1$)$_m$—, O, S, NR$^2$, —C(O)—, —O—C(O)—, —C(O)—O—, —O—C(O)—NR$^2$—, —C(O)—NR$^2$—, —NR$^2$—C(O)—, —NR$^2$—C(O)—O—, —NR$^2$—C(O)—NR$^2$—, —NR$^2$—SO$_2$—, —SO—, or —SO$_2$—; $R^{1e}$ and $R^{1f}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; m is 1-3; $R^2$ is hydrogen, $C_1$-$C_3$ alkyl or $C_1$-$C_3$ haloalkyl; $R^{1a}$, $R^{1b}$, $R^{1c}$, and $R^{1d}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; Q is N or $CR^{3a}$; V is N or $CR^{3b}$; W is N or $CR^3$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is phenyl substituted with 0-2 substituents independently selected from fluoro, chloro, methoxyethyl, and cyano; Z is a bond; X is —(CR$^{1e}$R$^{1f}$)$_m$—, O, S, NR$^2$, —C(O)—, —O—C(O)—, —C(O)—O—, —O—C(O)—NR$^2$—, —C(O)—NR$^2$—, —NR—C(O)—, —NR$^2$—C(O)—O—, —NR$^2$—C(O)—NR$^2$—, —NR$^2$—SO$_2$—, —SO—, or —SO$_2$—; $R^{1e}$ and $R^{1f}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; m is 1-3; $R^2$ is hydrogen, $C_1$-$C_3$ alkyl or $C_1$-$C_3$ haloalkyl; $R^{1a}$, $R^{1b}$, $R^{1c}$, and $R^{1d}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; Q is N or $CR^{3a}$; V is N or $CR^{3b}$; W is N or $CR^{3c}$; wherein no more than one of Q, V and W is N; $R^{3a}$, $R^{3b}$ and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is pyridyl substituted with 0-2 substituents independently selected from fluoro, chloro, methoxyethyl, and cyano; Z is a bond; X is —(CR$^{1e}$R$^{1f}$)$_m$—, O, S, NR$^2$, —C(O)—, —O—C(O)—, —C(O)—O—, —O—C(O)—NR$^2$—, —C(O)—NR$^2$, —NR—C(O)—, —NR$^2$—C(O)—O—, —NR$^2$—C(O)—NR$^2$—, —NR$^2$—SO$_2$—, —SO—, or —SO$_2$—; $R^{1e}$ and $R^{1f}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; m is 1-3; $R^2$ is hydrogen, $C_1$-$C_3$ alkyl or $C_1$-$C_3$ haloalkyl; $R^{1a}$, $R^{1b}$, $R^{1c}$, and $R^{1d}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; Q is N or $CR^{3a}$; V is N or $CR^{3b}$; W is N or $CR^{3c}$; wherein no more than one of Q, V and W is N; $R^{3a}$, $R^{3b}$ and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl, heteroaryl, heterocycle, or cycloalkyl; Z is a bond; X is —(CR$^{1e}$R$^{1f}$)$_m$—, O, S, NR$^2$, —SO—, or —SO$_2$—; R$^{1e}$ and R$^{1f}$ are independently hydrogen, fluoro, or C$_1$-C$_3$ alkyl; R$^2$ is hydrogen, C$_1$-C$_3$ alkyl or C$_1$-C$_3$ fluoroalkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^3$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl; Z is a bond; X is —(CR$^{1e}$R$^{1f}$)$_m$—, O, S, NR$^2$, —SO—, or —SO$_2$—; R$^{1e}$ and R$^{1f}$ are independently hydrogen, fluoro, or C$_1$-C$_3$ alkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^3$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl with 0-3 substituents independently selected from halogen, cyano, C$_1$-C$_6$ alkyl, C$_1$-C$_6$ fluoroalkyl, C$_1$-C$_6$ alkoxy(C$_1$-C$_6$)alkyl, C$_1$-C$_6$ hydroxyalkyl, C$_1$-C$_6$ hydroxy(C$_1$-C$_6$)fluoroalkyl, C$_1$-C$_6$ alkoxy(C$_1$-C$_6$)fluoroalkyl, C$_1$-C$_6$ cyanoalkyl, C$_1$-C$_6$ cyanofluoroalkyl, C$_3$-C$_8$ cycloalkyl, C$_3$-C$_8$ fluorocycloalkyl, OR$^4$, and NR$^{5a}$R$^{5b}$; wherein R$^4$ is hydrogen, C$_1$-C$_6$ alkyl or C$_1$-C$_6$ fluoroalkyl; and R$^{5a}$ and R$^{5b}$ are each independently hydrogen, C$_1$-C$_6$ alkyl, C$_3$-C$_8$ cycloalkyl, or C$_1$-C$_6$ heteroalkyl; or R$^{5a}$ and R$^{5b}$ together with the nitrogen atom to which they are attached form a heterocycle; wherein each R$^{5a}$ and R$^{5b}$ are substituted with 0-3 fluorine atoms; Z is a bond; X is —(CR$^{1e}$R$^{1f}$)$_m$—, O, S, NR$^2$, —SO—, or —SO$_2$—; R$^{1e}$ and R$^{1f}$ are independently hydrogen, fluoro, or C$_1$-C$_3$ alkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^3$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$)alkyl, and OR$^4$; wherein R$^4$ is hydrogen, C$_1$-C$_3$ alkyl, or C$_1$-C$_3$ fluoroalkyl; Z is a bond; X is —(CR$^{1e}$R$^{1f}$)$_m$—, O, S, NR$^2$, —SO—, or —SO$_2$—; R$^{1e}$ and R$^{1f}$ are independently hydrogen, fluoro, or C$_1$-C$_3$ alkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^{3c}$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is heteroaryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$) alkyl, and OR$^4$; wherein R$^4$ is hydrogen, C$_1$-C$_3$ alkyl, or C$_1$-C$_3$ fluoroalkyl; Z is a bond; X is —(CR$^{1e}$R$^{1f}$)$_m$—, O, S, NR$^2$, —SO—, or —SO$_2$—; R$^{1e}$ and R$^{1f}$ are independently hydrogen, fluoro, or C$_1$-C$_3$ alkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^{3c}$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is phenyl substituted with 0-2 substituents independently selected from fluoro, chloro, methoxyethyl, and cyano; Z is a bond; X is —(CR$^{1e}$R$^{1f}$)$_m$—, O, S, NR$^2$, —SO—, or —SO$_2$—; R$^{1e}$ and R$^{1f}$ are independently hydrogen, fluoro, or C$_1$-C$_3$ alkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^3$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is pyridyl substituted with 0-2 substituents independently selected from fluoro, chloro, methoxyethyl, and cyano; Z is a bond; X is —(CR$^{1e}$R$^{1f}$)$_m$—, O, S, NR$^2$, —SO—, or —SO$_2$—; R$^{1e}$ and R$^{1f}$ are independently hydrogen, fluoro, or C$_1$-C$_3$ alkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^3$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl, heteroaryl, heterocycle, or cycloalkyl; Z is a bond; X is O, S, or NR$^2$; R$^2$ is hydrogen, C$_1$-C$_3$ alkyl or C$_1$-C$_3$ fluoroalkyl; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^3$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl; Z is a bond; X is O, S, or NR$^2$; R$^{1a}$, R$^{1b}$, R$^{1c}$, and R$^{1d}$ are each independently hydrogen, halogen, C$_1$-C$_3$ alkyl, C$_1$-C$_3$ alkoxy, C$_1$-C$_3$ haloalkyl, or C$_1$-C$_3$ haloalkoxy; Q is N or CR$^{3a}$; V is N or CR$^{3b}$; W is N or CR$^{3c}$; wherein no more than one of Q, V and W is N; R$^{3a}$, R$^{3b}$, and R$^c$ are hydrogen, cyano, halogen, C$_1$-C$_3$ alkyl, C$_1$-C$_3$ alkoxy, C$_1$-C$_3$ haloalkyl, or C$_1$-C$_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; Q is N or $CR^{3a}$; V is N or $CR^{3b}$; W is N or $CR^3$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; Q is N or $CR^{3a}$; V is N or $CR^{3b}$; W is N or $CR^{3c}$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; Q is N or $CR^{3a}$; V is N or $CR^{3b}$; W is N or $CR^{3c}$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is phenyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; Q is N or $CR^{3a}$; V is N or $CR^{3b}$; W is N or $CR^3$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is pyridyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen, halogen, $C_1$-$C_3$ alkyl, $C_1$-$C_3$ alkoxy, $C_1$-$C_3$ haloalkyl, or $C_1$-$C_3$ haloalkoxy; Q is N or $CR^{3a}$; V is N or $CR^{3b}$; W is N or $CR^3$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl, heteroaryl, heterocycle, or cycloalkyl; Z is a bond; X is O, S, or $NR^2$; $R^2$ is hydrogen, $C_1$-$C_3$ alkyl or $C_1$-$C_3$ fluoroalkyl; $R^{1a}$, $R^{1b}$, $R^{1c}$, and $R^{1d}$ are each independently hydrogen, fluoro, $C_1$-$C_3$ alkyl, or $C_1$-$C_3$ fluoroalkyl; Q is N or $CR^{3a}$; V is N or $CR^{3b}$; W is N or $CR^{3c}$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl; Z is a bond; X is O, S, or $NR^2$; $R^{1a}$, $R^{1b}$, $R^{1c}$, and $R^{1d}$ are each independently hydrogen, fluoro, $C_1$-$C_3$ alkyl, or $C_1$-$C_3$ fluoroalkyl; Q is N or $CR^{3a}$; V is N or $CR^{3b}$; W is N or $CR^3$; wherein no more than one of Q, V and W is N; $R^{3a}R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen, fluoro, $C_1$-$C_3$ alkyl, or $C_1$-$C_3$ fluoroalkyl; Q is N or $CR^{3a}$; V is N or $CR^{3b}$; W is N or $CR^{3c}$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen, fluoro, $C_1$-$C_3$ alkyl, or $C_1$-$C_3$ fluoroalkyl; Q is N or $CR^{3a}$; V is N or $CR^{3b}$; W is N or $CR^{3c}$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen, fluoro, $C_1$-$C_3$ alkyl, or $C_1$-$C_3$ fluoroalkyl; Q is N or $CR^{3a}$; V is N or $CR^{3b}$; W is N or $CR^{3c}$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is phenyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen, fluoro, $C_1$-$C_3$ alkyl, or $C_1$-$C_3$ fluoroalkyl; Q is N or $CR^{3a}$; V is N or $CR^{3b}$; W is N or $CR^3$; wherein no more than one of Q, V and W is N; $R^{3a}R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is pyridyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen, fluoro, $C_1$-$C_3$ alkyl, or $C_1$-$C_3$ fluoroalkyl; Q is N or $CR^{3a}$; V is N or $CR^{3b}$; W is N or $CR^3$; wherein no more than one of Q, V and W is N; $R^{3a}R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl, heteroaryl, heterocycle, or cycloalkyl; Z is a bond; X is O, S, or $NR^2$; $R^2$ is hydrogen, $C_1$-$C_3$ alkyl or $C_1$-$C_3$ fluoroalkyl; $R^{1a}$, $R^{1b}$, $R^{1c}$, and $R^{1d}$ are each independently hydrogen or $C_1$-$C_3$ alkyl; Q is N or $CR^{3a}$; V is N or $CR^{3b}$; W is N or $CR^{3c}$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl; Z is a bond; X is O, S, or $NR^2$; $R^{1a}$, $R^{1b}$, $R^{1c}$, and $R^{1d}$ are each independently hydrogen or $C_1$-$C_3$ alkyl; Q is N or $CR^{3a}$; V is N or $CR^{3b}$; W is N or $CR^{3c}$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_5$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen or $C_1$-$C_3$ alkyl; Q is N or $CR^{3a}$; V is N or $CR^{3b}$; W is N or $CR^{3c}$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; Q is N or $CR^{3a}$; V is N or $CR^{3b}$; W is N or $CR^3$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; Q is N or $CR^{3a}$; V is N or $CR^{3b}$; W is N or $CR^3$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is phenyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; Q is N or $CR^{3a}$; V is N or $CR^{3b}$; W is N or $CR^{3c}$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is pyridyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; Q is N or $CR^{3a}$; V is N or $CR^{3b}$; W is N or $CR^{3c}$; wherein no more than one of Q, V and W is N; $R^{3a}$, $R^{3b}$, and $R^c$ are hydrogen, cyano, halogen, $C_1$-$C_3$ alkyl, $C_1$-$C_3$ alkoxy, $C_1$-$C_3$ haloalkyl, or $C_1$-$C_3$ haloalkoxy; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O; $R^{1a}$, $R^{1b}$, $R^{1c}$, and $R^{1d}$ are each independently hydrogen or $C_1$-$C_3$ alkyl; Q is N or $CR^{3a}$; V is $CR^{3b}$; W is $CR^{3c}$; $R^{3a}$, $R^{3b}$ and $R^{3c}$ are hydrogen, fluoro, $C_1$-$C_3$ alkyl, $C_1$-$C_3$ alkoxy, or $C_1$-$C_3$ fluoroalkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O; $R^{1a}$, $R^{1b}$, $R^{1c}$, and $R^{1d}$ are each independently hydrogen or $C_1$-$C_3$ alkyl; Q is N or $CR^{3a}$; V is $CR^{3b}$; W is $CR^{3c}$; $R^{3a}$, $R^{3b}$ and $R^{3c}$ are hydrogen, fluoro, $C_1$-$C_3$ alkyl, $C_1$-$C_3$ alkoxy, or $C_1$-$C_3$ fluoroalkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is phenyl substituted with 0-2 substituents independently selected from fluoro, chloro, methoxyethyl, and cyano; Z is a bond; X is O; $R^{1a}$, $R^{1b}$, $R^{1c}$, and $R^{1d}$ are each independently hydrogen or $C_1$-$C_3$ alkyl; Q is N or $CR^{3a}$; V is $CR^{3b}$; W is $CR^3$; $R^{3a}$, $R^{3b}$ and $R^{3c}$ are hydrogen, fluoro, $C_1$-$C_3$ alkyl, $C_1$-$C_3$ alkoxy, or $C_1$-$C_3$ fluoroalkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is pyridyl substituted with 0-2 substituents independently selected from fluoro, chloro, methoxyethyl, and cyano; Z is a bond; X is O; $R^{1a}$, $R^{1b}$, $R^{1c}$, and $R^{1d}$ are each independently hydrogen or $C_1$-$C_3$ alkyl; Q is N or $CR^{3a}$; V is $CR^{3b}$; W is $CR^3$; $R^{3a}$, $R^{3b}$ and $R^{3c}$ are hydrogen, fluoro, $C_1$-$C_3$ alkyl, $C_1$-$C_3$ alkoxy, or $C_1$-$C_3$ fluoroalkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is phenyl substituted with 0-2 substituents independently selected from fluoro, chloro, methoxyethyl, and cyano; Z is a bond; X is O; $R^{1a}$, $R^{1b}$, $R^{1c}$, and $R^{1d}$ are each independently hydrogen or $C_1$-$C_3$ alkyl; Q is N or $CR^{3a}$; V is $CR^{3b}$; W is $CR^{3c}$; $R^{3a}$, $R^{3b}$ and $R^{3c}$ are hydrogen, fluoro, $C_1$-$C_3$ alkyl, $C_1$-$C_3$ alkoxy, or $C_1$-$C_3$ fluoroalkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is pyridyl substituted with 0-2 substituents independently selected from fluoro, chloro, methoxyethyl, and cyano; Z is a bond; X is O; $R^{1a}$, $R^{1b}$, $R^{1c}$, and Rid are each independently hydrogen or $C_1$-$C_3$ alkyl; Q is N or $CR^{3a}$; V is $CR^{3b}$; W is $CR^3$; $R^{3a}$, $R^{3b}$ and $R^{3c}$ are hydrogen, fluoro, $C_1$-$C_3$ alkyl, $C_1$-$C_3$ alkoxy, or $C_1$-$C_3$ fluoroalkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In another aspect, the compound of formula (I) is a compound of formula (I-a):

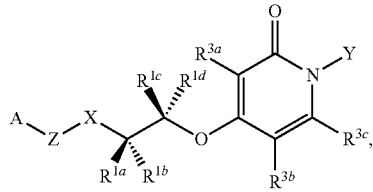

(I-a)

wherein A is aryl, heteroaryl, heterocycle, or cycloalkyl; Z is a bond; X is O, S, or $NR^2$; $R^2$ is hydrogen, $C_1$-$C_3$ alkyl or $C_1$-$C_3$ fluoroalkyl; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and Rid are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is phenyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and Rid are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is pyridyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and Rid are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl, heteroaryl, heterocycle, or cycloalkyl; Z is a bond; X is O, S, or $NR^2$; $R^2$ is hydrogen, $C_1$-$C_3$ alkyl or $C_1$-$C_3$ fluoroalkyl; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is aryl or heteroaryl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_5$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and Rid are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is phenyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is pyridyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and Rid are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is aryl, heteroaryl, heterocycle, or cycloalkyl; Z is a bond; X is O, S, or $NR^2$; $R^2$ is hydrogen, $C_1$-$C_3$ alkyl or $C_1$-$C_3$ fluoroalkyl; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl or heteroaryl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_5$ cycloalkyl, $C_3$-$C_5$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_5$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and Rid are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is phenyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is pyridyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and Rid are each independently hydrogen or $C_1$-$C_3$ alkyl; $R^{3a}$, $R^{3b}$, and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl, heteroaryl, heterocycle, or cycloalkyl; Z is a bond; X is O, S, or $NR^2$; $R^2$ is hydrogen, $C_1$-$C_3$ alkyl or $C_1$-$C_3$ fluoroalkyl; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl or heteroaryl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$, $R^{3b}$, and $R^{3c}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)

alkyl, and OR$^4$; wherein R$^4$ is hydrogen, C$_1$-C$_3$ alkyl, or C$_1$-C$_3$ fluoroalkyl; Z is a bond; X is O, S, or NR$^2$; R$^{1a}$, R$^{1b}$, R$^{1c}$, and Rid are each independently hydrogen or C$_1$-C$_3$ alkyl; R$^{3a}$, R$^{3b}$, and R$^{3c}$ are hydrogen, halogen, or C$_1$-C$_3$ alkyl; and Y is heteroaryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$)alkyl, and OR$^4$; wherein R$^4$ is hydrogen, C$_1$-C$_3$ alkyl, or C$_1$-C$_3$ fluoroalkyl.

In certain embodiments, A is heteroaryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$) alkyl, and OR$^4$; wherein R$^4$ is hydrogen, C$_1$-C$_3$ alkyl, or C$_1$-C$_3$ fluoroalkyl; Z is a bond; X is O, S, or NR$^2$; R$^{1a}$, R$^{1b}$, R$^{1c}$, and R$^{1d}$ are each independently hydrogen or C$_1$-C$_3$ alkyl; R$^{3a}$, R$^{3b}$, and R$^{3c}$ are hydrogen, halogen, or C$_1$-C$_3$ alkyl; and Y is heteroaryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$)alkyl, and OR$^4$; wherein R$^4$ is hydrogen, C$_1$-C$_3$ alkyl, or C$_1$-C$_3$ fluoroalkyl.

In certain embodiments, A is phenyl substituted with 0-2 substituents independently selected from fluoro, chloro, methoxyethyl, and cyano; Z is a bond; X is O, S, or NR$^2$; R$^{1a}$, R$^{1b}$, R$^{1c}$, and Rid are each independently hydrogen or C$_1$-C$_3$ alkyl; R$^{3a}$, R$^{3b}$, and R$^{3c}$ are hydrogen, halogen, or C$_1$-C$_3$ alkyl; and Y is heteroaryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$)alkyl, and OR$^4$; wherein R$^4$ is hydrogen, C$_1$-C$_3$ alkyl, or C$_1$-C$_3$ fluoroalkyl.

In certain embodiments, A is pyridyl substituted with 0-2 substituents independently selected from fluoro, chloro, methoxyethyl, and cyano; Z is a bond; X is O, S, or NR$^2$; R$^{1a}$, R$^{1b}$, R$^{1c}$, and R$^{1d}$ are each independently hydrogen or C$_1$-C$_3$ alkyl; R$^{3a}$, R$^{3b}$, and R$^{3c}$ are hydrogen, halogen, or C$_1$-C$_3$ alkyl; and Y is heteroaryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$)alkyl, and OR$^4$; wherein R$^4$ is hydrogen, C$_1$-C$_3$ alkyl, or C$_1$-C$_3$ fluoroalkyl.

In another aspect, the compound of formula (I) is a compound of formula (I-b):

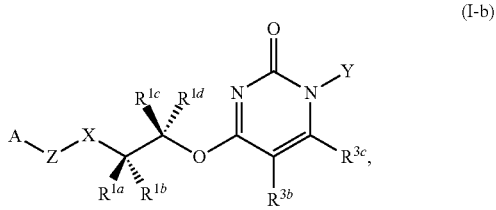

(I-b)

wherein A is aryl, heteroaryl, heterocycle, or cycloalkyl; Z is a bond; X is O, S, or NR$^2$; R$^2$ is hydrogen, C$_1$-C$_3$ alkyl or C$_1$-C$_3$ fluoroalkyl; R$^{1a}$, R$^{1b}$, R$^{1c}$, and R$^{1d}$ are each independently hydrogen or C$_1$-C$_3$ alkyl; R$^{3a}$, R$^{3b}$, and R$^{3c}$ are hydrogen, halogen, or C$_1$-C$_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl; Z is a bond; X is O, S, or NR$^2$; R$^{1a}$, R$^{1b}$, R$^{1c}$, and R$^{1d}$ are each independently hydrogen or C$_1$-C$_3$ alkyl; R$^{3b}$ and R$^{3c}$ are hydrogen, halogen, or C$_1$-C$_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl with 0-3 substituents independently selected from halogen, cyano, C$_1$-C$_6$ alkyl, C$_1$-C$_6$ fluoroalkyl, C$_1$-C$_6$ alkoxy(C$_1$-C$_6$)alkyl, C$_1$-C$_6$ hydroxyalkyl, C$_1$-C$_6$ hydroxy(C$_1$-C$_6$)fluoroalkyl, C$_1$-C$_6$ alkoxy(C$_1$-C$_6$)fluoroalkyl, C$_1$-C$_6$ cyanoalkyl, C$_1$-C$_6$ cyanofluoroalkyl, C$_3$-C$_8$ cycloalkyl, C$_3$-C$_5$ fluorocycloalkyl, OR$^4$, and NR$^{5a}$R$^{5b}$; wherein R$^4$ is hydrogen, C$_1$-C$_6$ alkyl or C$_1$-C$_6$ fluoroalkyl; and R$^{5a}$ and R$^{5b}$ are each independently hydrogen, C$_1$-C$_6$ alkyl, C$_3$-C$_8$ cycloalkyl, or C$_1$-C$_6$ heteroalkyl; or R$^{5a}$ and R$^{5b}$ together with the nitrogen atom to which they are attached form a heterocycle; wherein each R$^{5a}$ and R$^{5b}$ are substituted with 0-3 fluorine atoms; Z is a bond; X is O, S, or NR$^2$; R$^{1a}$, R$^{1b}$, R$^{1c}$, and R$^{1d}$ are each independently hydrogen or C$_1$-C$_3$ alkyl; R$^{3b}$ and R$^{3c}$ are hydrogen, halogen, or C$_1$-C$_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$) alkyl, and OR$^4$; wherein R$^4$ is hydrogen, C$_1$-C$_3$ alkyl, or C$_1$-C$_3$ fluoroalkyl; Z is a bond; X is O, S, or NR$^2$; R$^{1a}$, R$^{1b}$, R$^{1c}$, and R$^{1d}$ are each independently hydrogen or C$_1$-C$_3$ alkyl; R$^{3b}$ and R$^{3c}$ are hydrogen, halogen, or C$_1$-C$_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is heteroaryl substituted with 0-3 substituents independently selected from fluoro, chloro, cyano, C$_1$-C$_3$ alkyl, C$_1$-C$_3$ fluoroalkyl, C$_1$-C$_3$ alkoxy(C$_1$-C$_3$) alkyl, and OR$^4$; wherein R$^4$ is hydrogen, C$_1$-C$_3$ alkyl, or C$_1$-C$_3$ fluoroalkyl; Z is a bond; X is O, S, or NR$^2$; R$^{1a}$, R$^{1b}$, R$^{1c}$, and R$^{1d}$ are each independently hydrogen or C$_1$-C$_3$ alkyl; R$^{3b}$ and R$^{3c}$ are hydrogen, halogen, or C$_1$-C$_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is phenyl substituted with 0-2 substituents independently selected from fluoro, chloro, methoxyethyl, and cyano; Z is a bond; X is O, S, or NR$^2$; R$^{1a}$, R$^{1b}$, R$^{1c}$, and R$^{1d}$ are each independently hydrogen or C$_1$-C$_3$ alkyl; R$^{3b}$ and R$^{3c}$ are hydrogen, halogen, or C$_1$-C$_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is pyridyl substituted with 0-2 substituents independently selected from fluoro, chloro, methoxyethyl, and cyano; Z is a bond; X is O, S, or NR$^2$; R$^{1a}$, R$^{1b}$, R$^{1c}$, and R$^{1d}$ are each independently hydrogen or C$_1$-C$_3$ alkyl; R$^{3b}$ and R$^{3c}$ are hydrogen, halogen, or C$_1$-C$_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl, heteroaryl, heterocycle, or cycloalkyl; Z is a bond; X is O, S, or NR$^2$; R$^2$ is hydrogen, C$_1$-C$_3$ alkyl or C$_1$-C$_3$ fluoroalkyl; R$^{1a}$, R$^{1b}$, R$^{1c}$, and R$^{1d}$ are each independently hydrogen or C$_1$-C$_3$ alkyl; R$^{3b}$ and R$^{3c}$ are hydrogen, halogen, or C$_1$-C$_3$ alkyl; and Y is aryl or heteroaryl, with 0-3 substituents independently selected from halogen, cyano, C$_1$-C$_6$ alkyl, C$_1$-C$_6$ fluoroalkyl, C$_1$-C$_6$ alkoxy(C$_1$-C$_6$)alkyl, C$_1$-C$_6$ hydroxy(C$_1$-C$_6$)alkyl, C$_1$-C$_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is aryl or heteroaryl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is phenyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is pyridyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is aryl, heteroaryl, heterocycle, or cycloalkyl; Z is a bond; X is O, S, or $NR^2$; $R^2$ is hydrogen, $C_1$-$C_3$ alkyl or $C_1$-$C_3$ fluoroalkyl; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl or heteroaryl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is phenyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is pyridyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl, heteroaryl, heterocycle, or cycloalkyl; Z is a bond; X is O, S, or $NR^2$; $R^2$ is hydrogen, $C_1$-$C_3$ alkyl or $C_1$-$C_3$ fluoroalkyl; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl or heteroaryl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is phenyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3b}$ and $R^{3c}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and OR$^4$; wherein R$^4$ is hydrogen, $C_1$-$C_3$ alkyl, or $C_1$-$C_3$ fluoroalkyl.

In certain embodiments, A is pyridyl substituted with 0-2 substituents independently selected from fluoro, chloro, methoxyethyl, and cyano; Z is a bond; X is O, S, or NR$^2$; R$^{1a}$, R$^{1b}$, R$^{1c}$, and R$^{1d}$ are each independently hydrogen or $C_1$-$C_3$ alkyl; R$^{3b}$ and R$^{3c}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and OR$^4$; wherein R$^4$ is hydrogen, $C_1$-$C_3$ alkyl, or $C_1$-$C_3$ fluoroalkyl.

In another aspect, the compound of formula (I) is a compound of formula (I-c):

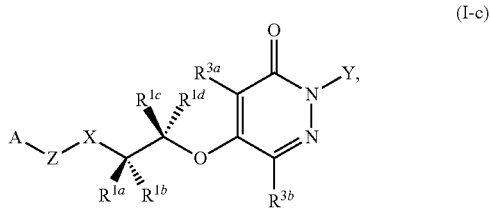

(I-c)

wherein A is aryl, heteroaryl, heterocycle, or cycloalkyl; Z is a bond; X is O, S, or NR$^2$; R$^2$ is hydrogen, $C_1$-$C_3$ alkyl or $C_1$-$C_3$ fluoroalkyl; R$^{1a}$, R$^{1b}$, R$^{1c}$, and R$^{1d}$ are each independently hydrogen or $C_1$-$C_3$ alkyl; R$^{3a}$ and R$^{3b}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl; Z is a bond; X is O, S, or NR$^2$; R$^{1a}$, R$^{1b}$, R$^{1c}$, and R$^{1d}$ are each independently hydrogen or $C_1$-$C_3$ alkyl; R$^{3a}$ and R$^{3b}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_5$ fluorocycloalkyl, OR$^4$, and NR$^{5a}$R$^{5b}$; wherein R$^4$ is hydrogen, $C_1$-$C_6$ alkyl or $C_1$-$C_6$ fluoroalkyl; and R$^{5a}$ and R$^{5b}$ are each independently hydrogen, $C_1$-$C_6$ alkyl, $C_3$-$C_8$ cycloalkyl, or $C_1$-$C_6$ heteroalkyl; or R$^{5a}$ and R$^{5b}$ together with the nitrogen atom to which they are attached form a heterocycle; wherein each R$^{5a}$ and R$^{5b}$ are substituted with 0-3 fluorine atoms; Z is a bond; X is O, S, or NR$^2$; R$^{1a}$, R$^{1b}$, R$^{1c}$, and R$^{1d}$ are each independently hydrogen or $C_1$-$C_3$ alkyl; R$^{3a}$ and R$^{3b}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and OR$^4$; wherein R$^4$ is hydrogen, $C_1$-$C_3$ alkyl, or $C_1$-$C_3$ fluoroalkyl; Z is a bond; X is O, S, or NR$^2$; R$^{1a}$, R$^{1b}$, R$^{1c}$, and R$^{1d}$ are each independently hydrogen or $C_1$-$C_3$ alkyl; R$^{3a}$ and R$^{3b}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and OR$^4$; wherein R$^4$ is hydrogen, $C_1$-$C_3$ alkyl, or $C_1$-$C_3$ fluoroalkyl; Z is a bond; X is O, S, or NR$^2$; R$^{1a}$, R$^{1b}$, R$^{1c}$, and R$^{1d}$ are each independently hydrogen or $C_1$-$C_3$ alkyl; R$^{3a}$ and R$^{3b}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is phenyl substituted with 0-2 substituents independently selected from fluoro, chloro, methoxyethyl, and cyano; Z is a bond; X is O, S, or NR$^2$; R$^{1a}$, R$^{1b}$, R$^{1c}$, and R$^{1d}$ are each independently hydrogen or $C_1$-$C_3$ alkyl; R$^{3a}$ and R$^{3b}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is pyridyl substituted with 0-2 substituents independently selected from fluoro, chloro, methoxyethyl, and cyano; Z is a bond; X is O, S, or NR$^2$; R$^{1a}$, R$^{1b}$, R$^{1c}$, and R$^{1d}$ are each independently hydrogen or $C_1$-$C_3$ alkyl; R$^{3a}$ and R$^{3b}$ are hydrogen, halogen, or $C_1$-$C_3$ alkyl; and Y is aryl, heteroaryl, cycloalkyl, or heterocycle; wherein said aryl, heteroaryl, cycloalkyl, and heterocycle, at each occurrence, are independently substituted or unsubstituted.

In certain embodiments, A is aryl, heteroaryl, heterocycle, or cycloalkyl; Z is a bond; X is O, S, or NR$^2$; R$^2$ is hydrogen, $C_1$-$C_3$ alkyl or $C_1$-$C_3$ fluoroalkyl; R$^{1a}$, R$^{1b}$, R$^{1c}$, and R$^{1d}$ are each independently hydrogen or $C_1$-$C_3$ alkyl; R$^{3a}$ and R$^{3b}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, OR$^4$, and NR$^{5a}$R$^{5b}$; wherein R$^4$ is hydrogen, $C_1$-$C_6$ alkyl or $C_1$-$C_6$ fluoroalkyl; and R$^{5a}$ and R$^{5b}$ are each independently hydrogen, $C_1$-$C_6$ alkyl, $C_3$-$C_8$ cycloalkyl, or $C_1$-$C_6$ heteroalkyl; or R$^{5a}$ and R$^{5b}$ together with the nitrogen atom to which they are attach form a heterocycle; wherein each R$^{5a}$ and R$^{5b}$ are substituted with 0-3 fluorine atoms.

In certain embodiments, A is aryl or heteroaryl; Z is a bond; X is O, S, or NR$^2$; R$^{1a}$, R$^{1b}$, R$^{1c}$, and R$^{1d}$ are each independently hydrogen or $C_1$-$C_3$ alkyl; R$^{3a}$ and R$^{3b}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, OR$^4$, and NR$^{5a}$R$^{5b}$; wherein R$^4$ is hydrogen, $C_1$-$C_6$ alkyl or $C_1$-$C_6$ fluoroalkyl; and R$^{5a}$ and R$^{5b}$ are each independently hydrogen, $C_1$-$C_6$ alkyl, $C_3$-$C_8$ cycloalkyl, or $C_1$-$C_6$ heteroalkyl; or R$^{5a}$ and R$^{5b}$ together with the nitrogen atom to which they are attach form a heterocycle; wherein each R$^{5a}$ and R$^{5b}$ are substituted with 0-3 fluorine atoms.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is phenyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is pyridyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is aryl or heteroaryl, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle; wherein each $R^{5a}$ and $R^{5b}$ are substituted with 0-3 fluorine atoms.

In certain embodiments, A is aryl, heteroaryl, heterocycle, or cycloalkyl; Z is a bond; X is O, S, or $NR^2$; $R^2$ is hydrogen, $C_1$-$C_3$ alkyl or $C_1$-$C_3$ fluoroalkyl; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl or heteroaryl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_5$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is phenyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is pyridyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl, heteroaryl, heterocycle, or cycloalkyl; Z is a bond; X is O, S, or $NR^2$; $R^2$ is hydrogen, $C_1$-$C_3$ alkyl or $C_1$-$C_3$ fluoroalkyl; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl or heteroaryl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl or heteroaryl with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxyalkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_5$ cycloalkyl, $C_3$-$C_5$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_5$ cycloalkyl, or $C_1$-$C_6$ heteroalkyl; or $R^{5a}$ and $R^{5b}$ together with the nitrogen atom to which they are attached form a heterocycle; wherein each $R^{5a}$ and $R^{5b}$ are substituted with 0-3 fluorine atoms; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is aryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is phenyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

In certain embodiments, A is pyridyl substituted with 0-2 substituents independently selected from fluoro, chloro, methoxyethyl, and cyano; Z is a bond; X is O, S, or $NR^2$; $R^{1a}$, $R^{1b}$, $R^{1c}$, and $R^{1d}$ are each independently hydrogen or $C_1$-$C_3$ alkyl; $R^{3a}$ and $R^{3b}$ are hydrogen, halogen, or $C_1$-$C_3$ alkyl; and Y is heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

Representative compounds of formula (I) include, but are not limited to:

1-(4-fluorophenyl)-4-(3-phenylpropoxy)pyridin-2(1H)-one;
1-(4-fluorophenyl)-4-(2-phenoxyethoxy)pyridin-2(1H)-one;
1-(4-fluorophenyl)-4-(2-(phenylthio)ethoxy)pyridin-2(1H)-one;
1-(4-fluorophenyl)-4-(2-(methyl(phenyl)amino)ethoxy) pyridin-2(1H)-one;
1-(3-fluorophenyl)-4-(2-phenoxyethoxy)pyridin-2(1H)-one;
1-(2-fluorophenyl)-4-(2-phenoxyethoxy)pyridin-2(1H)-one;
1-(3,4-difluorophenyl)-4-(2-phenoxyethoxy)pyridin-2(1H)-one;
1-(3,5-difluorophenyl)-4-(2-phenoxyethoxy)pyridin-2(1H)-one;
3-(2-oxo-4-(2-phenoxyethoxy)pyridin-1(2H)-yl)benzonitrile;
3-fluoro-5-(2-oxo-4-(2-phenoxyethoxy)pyridin-1(2H)-yl) benzonitrile;

4-(2-oxo-4-(2-phenoxyethoxy)pyridin-1(2H)-yl)benzonitrile;
4-(2-phenoxyethoxy)-2H-[1,2'-bipyridin]-2-one;
6'-fluoro-4-(2-phenoxyethoxy)-2H-[1,2'-bipyridin]-2-one;
6'-fluoro-4-(2-phenoxyethoxy)-2H-[1,3'-bipyridin]-2-one;
4-(2-phenoxyethoxy)-2H-[1,4'-bipyridin]-2-one;
4-(2-(2-fluorophenoxy)ethoxy)-1-(4-fluorophenyl)pyridin-2(1H)-one;
4-(2-(3-fluorophenoxy)ethoxy)-1-(4-fluorophenyl)pyridin-2(1H)-one;
4-(2-(4-fluorophenoxy)ethoxy)-1-(4-fluorophenyl)pyridin-2(1H)-one;
4-(2-(2,3-difluorophenoxy)ethoxy)-1-(4-fluorophenyl)pyridin-2(1H)-one;
4-(2-(2,4-difluorophenoxy)ethoxy)-1-(4-fluorophenyl)pyridin-2(1H)-one;
4-(2-(2,5-difluorophenoxy)ethoxy)-1-(4-fluorophenyl)pyridin-2(1H)-one;
4-(2-(2,6-difluorophenoxy)ethoxy)-1-(4-fluorophenyl)pyridin-2(1H)-one;
4-(2-(2-chlorophenoxy)ethoxy)-1-(4-fluorophenyl)pyridin-2(1H)-one;
4-(2-(3-chlorophenoxy)ethoxy)-1-(4-fluorophenyl)pyridin-2(1H)-one;
4-(2-(4-chlorophenoxy)ethoxy)-1-(4-fluorophenyl)pyridin-2(1H)-one;
1-(4-fluorophenyl)-4-(2-((2-fluoropyridin-3-yl)oxy)ethoxy)pyridin-2(1H)-one;
3-(2-((1-(4-fluorophenyl)-2-oxo-1,2-dihydropyridin-4-yl)oxy)ethoxy)benzonitrile;
4-(2-((1-(4-fluorophenyl)-2-oxo-1,2-dihydropyridin-4-yl)oxy)ethoxy)benzonitrile;
1-(4-fluorophenyl)-4-(2-(4-(methoxymethyl)phenoxy)ethoxy)pyridin-2(1H)-one;
1-(4-fluorophenyl)-4-(2-(pyridin-3-yloxy)ethoxy)pyridin-2(1H)-one;
1-(4-fluorophenyl)-4-(2-((6-fluoropyridin-3-yl)oxy)ethoxy)pyridin-2(1H)-one;
4-(2-((5-chloropyridin-3-yl)oxy)ethoxy)-1-(4-fluorophenyl)pyridin-2(1H)-one;
4-(2-((4-chloropyridin-3-yl)oxy)ethoxy)-1-(4-fluorophenyl)pyridin-2(1H)-one;
4-(2-((2-chloropyridin-3-yl)oxy)ethoxy)-1-(4-fluorophenyl)pyridin-2(1H)-one;
1-(4-fluorophenyl)-4-(2-(pyridin-2-yloxy)ethoxy)pyridin-2(1H)-one;
1-(4-fluorophenyl)-4-(2-((3-fluoropyridin-2-yl)oxy)ethoxy)pyridin-2(1H)-one;
1-(4-fluorophenyl)-4-(2-((5-fluoropyridin-2-yl)oxy)ethoxy)pyridin-2(1H)-one;
4-(2-((6-chloropyridin-2-yl)oxy)ethoxy)-1-(4-fluorophenyl)pyridin-2(1H)-one;
4-(2-((3-chloropyridin-2-yl)oxy)ethoxy)-1-(4-fluorophenyl)pyridin-2(1H)-one;
4-(2-((4-chloropyridin-2-yl)oxy)ethoxy)-1-(4-fluorophenyl)pyridin-2(1H)-one;
4-(2-((5-chloropyridin-2-yl)oxy)ethoxy)-1-(4-fluorophenyl)pyridin-2(1H)-one;
2-(2-((1-(4-fluorophenyl)-2-oxo-1,2-dihydropyridin-4-yl)oxy)ethoxy)nicotinonitrile;
2-(2-((1-(4-fluorophenyl)-2-oxo-1,2-dihydropyridin-4-yl)oxy)ethoxy)isonicotinonitrile;
6-(2-((1-(4-fluorophenyl)-2-oxo-1,2-dihydropyridin-4-yl)oxy)ethoxy)nicotinonitrile;
6-(2-((1-(4-fluorophenyl)-2-oxo-1,2-dihydropyridin-4-yl)oxy)ethoxy)picolinonitrile
1-(4-fluorophenyl)-4-(2-phenoxyethoxy)pyrimidin-2(1H)-one;
1-(3-fluorophenyl)-4-(2-phenoxyethoxy)pyrimidin-2(1H)-one;
1-(3,4-difluorophenyl)-4-(2-phenoxyethoxy)pyrimidin-2(1H)-one;
1-(5-fluoropyridin-2-yl)-4-(2-phenoxyethoxy)pyrimidin-2(1H)-one;
3-(4-fluorophenyl)-6-(2-phenoxyethoxy)pyrimidin-4(3H)-one;
2-(4-fluorophenyl)-5-(2-phenoxyethoxy)pyridazin-3 (2H)-one;
2-oxo-4-(2-phenoxyethoxy)-2H-[1,3'-bipyridine]-5'-carbonitrile;
5'-fluoro-4-(2-phenoxyethoxy)-2H-[1,3'-bipyridin]-2-one;
1-(4-fluorophenyl)-4-(2-phenoxypropoxy)pyridin-2(1H)-one;
1-(4-fluorophenyl)-4-((1-phenoxypropan-2-yl)oxy)pyridin-2(1H)-one;
4-(2-(Benzyloxy)ethoxy)-1-(4-fluorophenyl)pyridin-2(1H)-one;
4-(2-(cyclopentyloxy)ethoxy)-1-(4-fluorophenyl)pyridin-2(1H)-one;
4-(2-(cyclohexyloxy)ethoxy)-1-(4-fluorophenyl)pyridin-2(1H)-one;
1-(4-fluorophenyl)-4-(2-(phenylsulfinyl)ethoxy)pyridin-2(1H)-one; and
1-(4-fluorophenyl)-4-(2-(phenylsulfonyl)ethoxy)pyridin-2(1H)-one; or pharmaceutically acceptable salts thereof.

Compound names are assigned by using Struct=Name naming algorithm as part of CHEMDRAW® ULTRA v. 12.0.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Allosteric Modulation of mGlu$_3$

The disclosed compounds may act or function as non-competitive antagonists, allosteric inhibitors, allosteric antagonists, or negative allosteric modulators (NAM) of mGlu$_3$. The compounds may be precognitive and neuroprotective even in the presence of mGlu$_3$ dysfunction.

Compounds of formula (I) can inhibit mGlu$_3$ with an IC$_{50}$ ranging from about 1 nM to about 30 μM. The compounds may have an IC$_{50}$ of about 30 μM, about 29 μM, about 28 μM, about 27 μM, about 26 μM, about 25 μM, about 24 μM, about 23 μM, about 22 μM, about 21 M, about 20 μM, about 19 μM, about 18 μM, about 17 μM, about 16 μM, about 15 μM, about 14 μM, about 13 μM, about 12 μM, about 11 μM, about 10 μM, about 9 μM, about 8 μM, about 7 μM, about 6 μM, about 5 μM, about 4 μM, about 3 μM, about 2 μM, about 1 μM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, or about 1 nM. Compounds of formula (I) can inhibit mGlu$_3$ with an IC50 of less than 30 μM, less than 29 μM, less than 28 μM, less than 27 M, less than 26 μM, less than 25 μM, less than 24 μM, less than 23 μM, less than 22 μM, less than 21 μM, less than 20 μM, less than 19 μM, less than 18 μM, less than 17 μM, less than 16 M, less than 15 μM, less than 14 μM, less than 13 μM, less than 12 μM, less than 11 μM, less than 10 μM, less than 9 μM, less than 8 μM, less than 7 μM, less than 6 μM, less than 5 μM, less than 4 μM, less than 3 μM, less than 2 μM, less than 1 μM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, or less than 1 nM.

Compounds of formula (I) may be selective modulators of mGlu$_3$ over mGlu$_2$. The compounds may have a ratio of mGlu$_3$ IC$_{50}$ to mGlu$_2$ IC$_{50}$ of at least 100, at least 95, at least 90, at least 85, at least 80, at least 75, at least 70, at least 64, at least 60, at least 55, at least 50, at least 45, at least 40, at least 35, at least 33, at least 31, at least 30, at least 29, at least 28, at least 27, at least 26, at least 25, at least 24, at least 23, at least 22, at least 21, at least 20, at least 19, at least 18, at least 17, at least 16, at least 15, at least 14, at least 13, at least 12, at least 11, at least 10, at least 9, at least 8, at least 7, at least 6, at least 5, at least 4, at least 3, or at least 2. Compounds of formula (I) may have a ratio of mGlu$_3$ IC$_{50}$ to mGlu$_2$ IC$_{50}$ of about 100, about 95, about 90, about 85, about 80, about 75, about 70, about 64, about 60, about 55, about 50, about 45, about 40, about 35, about 33, about 31, about 30, about 29, about 28, about 27, about 26, about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, or about 2.

Compounds of formula (I) may be selective modulators of mGlu$_3$ over mGlus. The compounds may have a ratio of mGlu$_3$ IC$_{50}$ to mGlu$_5$ EC$_{50}$ of at least 100, at least 95, at least 90, at least 85, at least 80, at least 75, at least 70, at least 64, at least 60, at least 55, at least 50, at least 45, at least 40, at least 35, at least 33, at least 31, at least 30, at least 29, at least 28, at least 27, at least 26, at least 25, at least 24, at least 23, at least 22, at least 21, at least 20, at least 19, at least 18, at least 17, at least 16, at least 15, at least 14, at least 13, at least 12, at least 11, at least 10, at least 9, at least 8, at least 7, at least 6, at least 5, at least 4, at least 3, or at least 2. Compounds of formula (I) may have a ratio of mGlu$_3$ IC$_{50}$ to mGlu$_5$ EC$_{50}$ of about 100, about 95, about 90, about 85, about 80, about 75, about 70, about 64, about 60, about 55, about 50, about 45, about 40, about 35, about 33, about 31, about 30, about 29, about 28, about 27, about 26, about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, or about 2.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

B. General Synthesis

Compounds of formula (I) may be prepared by synthetic processes or by metabolic processes. Preparation of the compounds by metabolic processes includes those occurring in the human or animal body (in vivo) or processes occurring in vitro.

Compounds of formula (I), wherein the groups A, X, $R^{1a}$, $R^{1b}$, $R^{1c}$, $R^{1d}$, Q, V, W and Y have the meanings as set forth in the Summary of the Invention section unless otherwise noted, can be synthesized as shown in Schemes 1-15.

Abbreviations which have been used in the descriptions of the Schemes that follow are: Ac$_2$O for acetic anhydride; D$^t$BAD for di-tert-butylazodicarboxylate; BuLi for butyllithium; DBU for 1,8-diazabicyclo[5.4.0]undec-7-ene; DMA for dimethylacetamide; DMF for dimethylformamide; DMSO for dimethylsulfoxide; MeOH for methanol; MS for molecular sieves; OAc for acetate; Pd/C for palladium on carbon; n-PrOH for n-propanol; PhMe for toluene; THF for tetrahydrofuran.

As shown in Scheme 1, intermediate v can be prepared from benzyl ether i, wherein $R^{3a}$, $R^{3b}$ and $R^{3c}$ are as defined in the Summary of the Invention. Reaction of i in a Chan-Lam coupling with a boronic ester (ii) or boronic acid (iii), wherein Y is as defined in the Summary of the Invention, can result in formation of intermediate iv. Removal of the benzyl group can be achieved with palladium on carbon under an atmosphere of hydrogen to afford intermediate v.

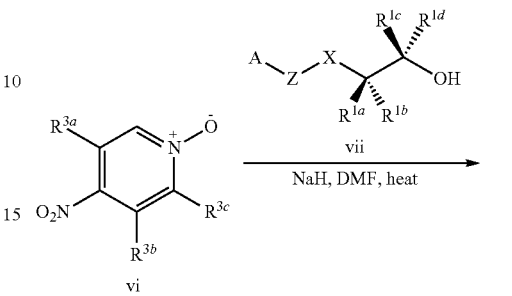

Scheme 2 illustrates the conversion of vi to intermediate ix. Nitropyridine oxide vi, wherein $R^{3a}$, $R^{3b}$ and $R^{3c}$ are as defined in the Summary of the Invention, can be treated with the sodium alkoxide generated in situ from alcohol vii, wherein A, Z, X, $R^{1a}$, $R^{1b}$, $R^{1c}$ and $R^{1d}$ are as defined in the Summary of the Invention, to provide intermediate ether viii. Intermediate viii can be treated with acetic anhydride and heating followed by aqueous hydroxide to afford intermediate ix.

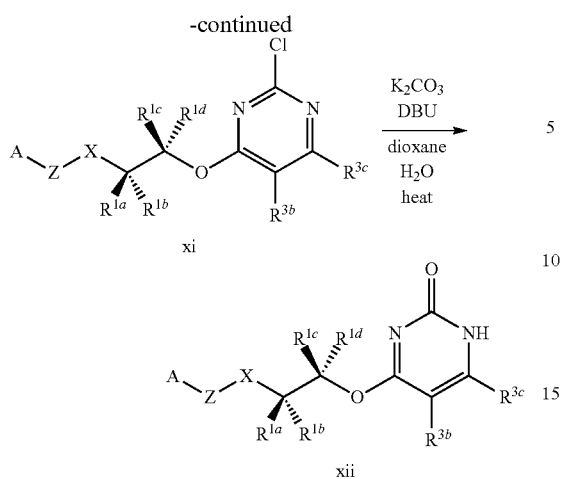

Scheme 5. Synthesis of intermediate xxi

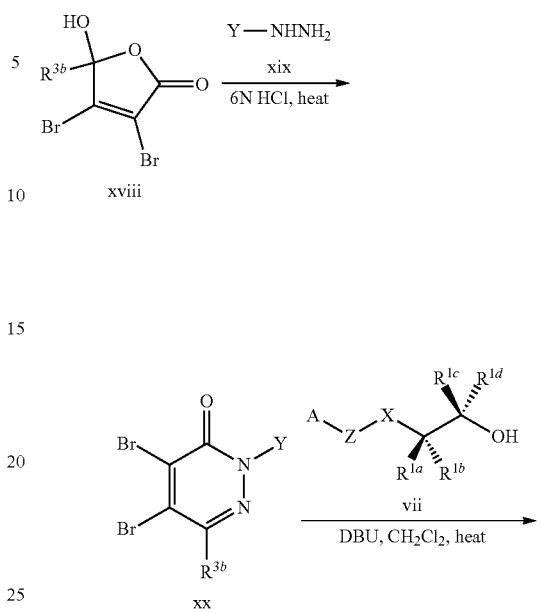

Scheme 3 depicts the preparation of intermediate xii from x. Dichloropyrimidine x, wherein $R^{3b}$ and $R^{3c}$ are as defined in the Summary of the Invention, can be treated with the sodium alkoxide generated in situ from alcohol vii to provide intermediate ether xi. Intermediate xi can be treated with base in the presence of water with heating to yield intermediate xii.

Scheme 4. Synthesis of intermediate xvii

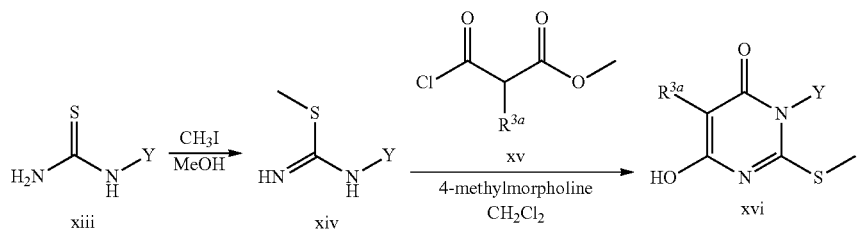

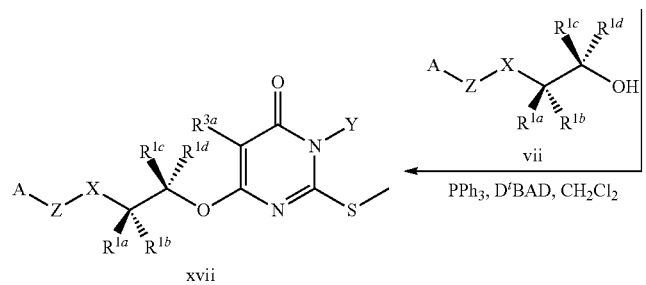

Scheme 4 demonstrates the conversion of xiii to intermediate xvii. Thiourea xiii, wherein Y is as defined in the Summary of the Invention, can be treated with methyl iodide to yield intermediate xiv. Intermediate xiv can be reacted with acid chloride xv, wherein $R^{3a}$ is as defined in the Summary of the Invention, to provide intermediate xvi. Intermediate xvi can be reacted with alcohol vii in a Mitsunobu reaction to afford intermediate xvii.

-continued

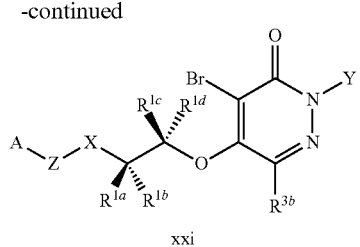

Scheme 5 illustrates the conversion of intermediate xviii to intermediate xxi. Furanone xviii, wherein $R^{3b}$ is as defined in the Summary of the Invention, can be reacted under acidic conditions with hydrazine xix, wherein Y is as defined in the Summary of the Invention, to provide intermediate xx. Intermediate xx can be treated with alcohol vii and a suitable base to provide intermediate ether xxi.

Scheme 6. Synthesis of intermediate xxiii

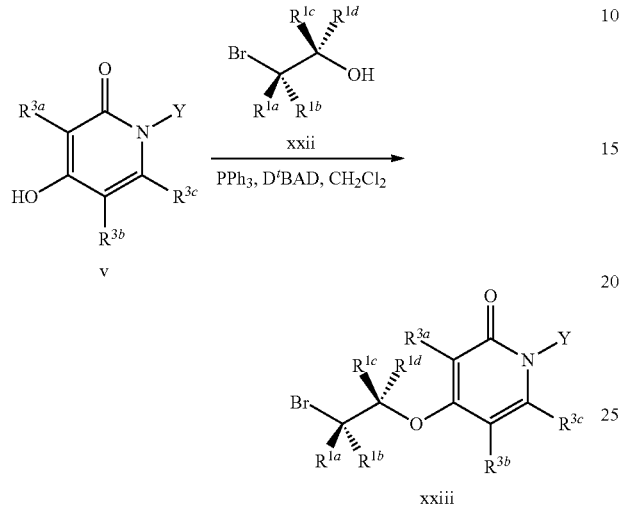

Scheme 6 shows the conversion of v to intermediate xxiii. Pyridone v, wherein $R^{3a}$, $R^{3b}$ and $R^{3c}$ are as defined in the Summary of the Invention, may be reacted with alcohol xxii, wherein $R^{1a}$, $R^{1b}$, $R^{1c}$ and $R^{1d}$ are as defined in the Summary of the Invention, in a Mitsunobu reaction to afford intermediate xxiii.

Scheme 7. Synthesis of intermediate xxvi

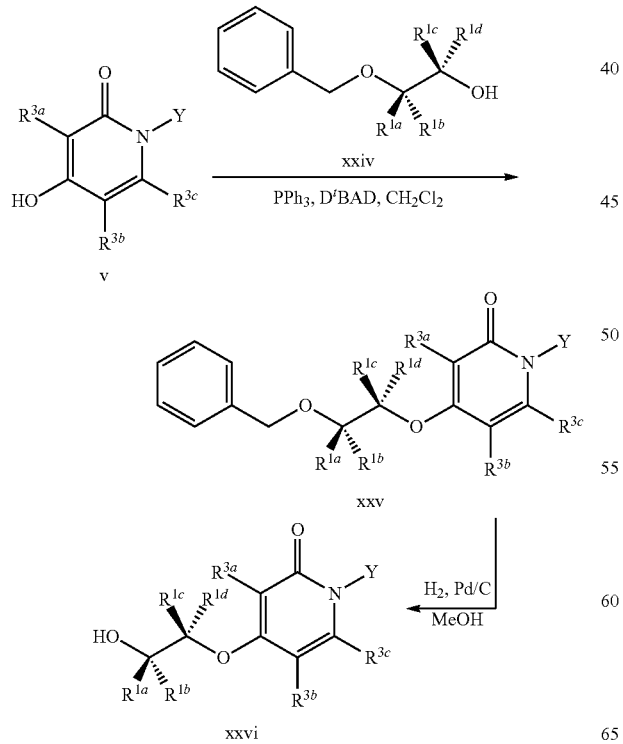

Scheme 7 illustrates the preparation of intermediate xxvi from intermediate v. Intermediate v may be reacted with alcohol xxiv, wherein $R^{1a}$, $R^{1b}$, $R^{1c}$ and $R^{1d}$ are as defined in the Summary of the Invention, in a Mitsunobu reaction to afford intermediate xxv. The benzyl group of xxv can be removed with palladium on carbon under an atmosphere of hydrogen to afford intermediate xxvi.

Scheme 8. Synthesis of the compound of formula (I)

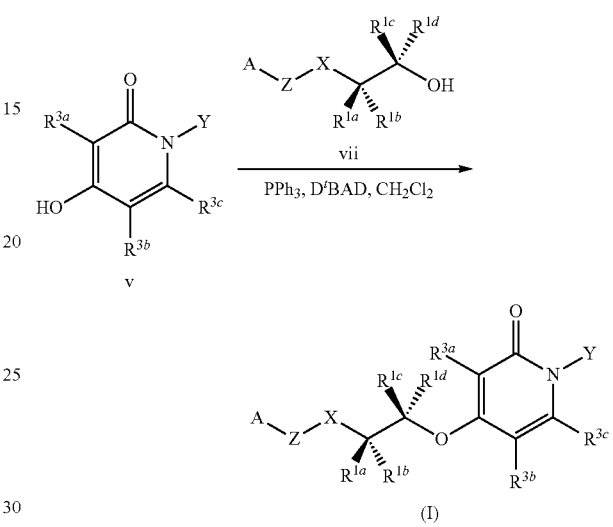

As illustrated in Scheme 8, the compound of formula (I) can be prepared from pyridone v. Reaction of intermediate v with alcohol vii in a Mitsunobu reaction can afford the compound of formula (I).

Scheme 9. Synthesis of the compound of formula (I)

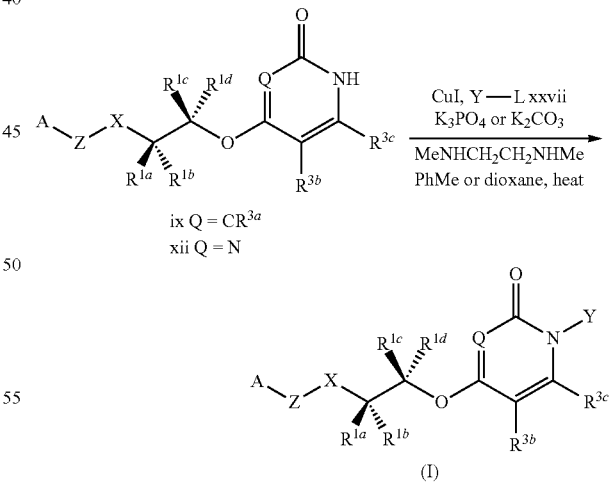

The compound of formula (I) can also be prepared from intermediate ix or intermediate xii, as shown in Scheme 9. Reaction of intermediate ix or intermediate xii in a copper promoted coupling with starting material xxvii, wherein L is Cl, Br, I, or $OSO_2CF_3$ and wherein Y is as defined in the Summary of the Invention, can afford the compound of formula (I).

Scheme 10. Synthesis of the compound of formula (I)

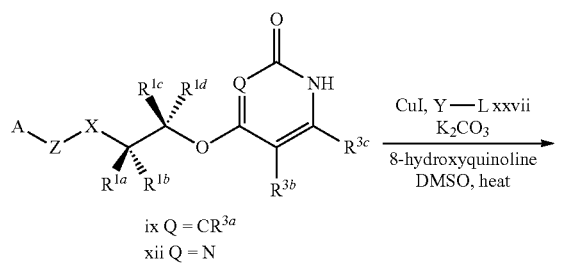

ix Q = CR$^{3a}$
xii Q = N

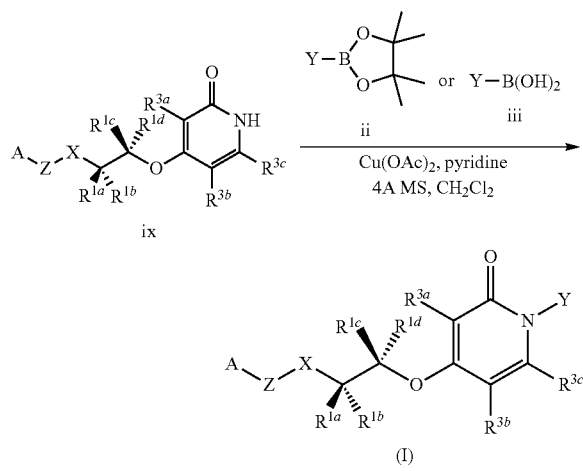

(I)

As illustrated in Scheme 10, the compound of formula (I) can also be prepared from intermediate ix or intermediate xii under alternative conditions. Reaction of intermediate ix or intermediate xii in a copper promoted coupling with starting material xxvii can afford the compound of formula (I).

Scheme 11. Synthesis of the compound of formula (I)

ix (I)

The compound of formula (I) can also be prepared from intermediate ix, as demonstrated in Scheme 11. Reaction of intermediate ix in a Chan-Lam coupling with starting materials ii or iii can afford the compound of formula (I).

Scheme 12. Synthesis of the compound of formula (I)

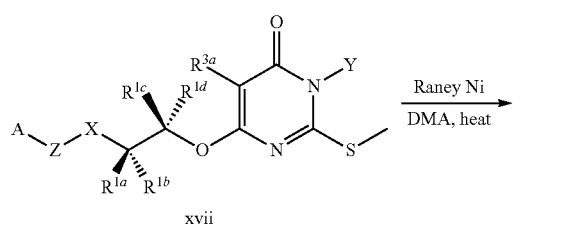

xvii

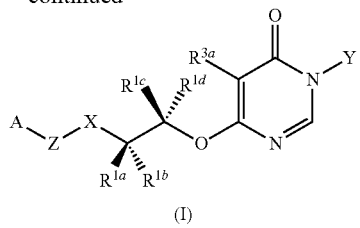

(I)

As illustrated in Scheme 12, the compound of formula (I) can be prepared from intermediate xvii. Reaction of intermediate xvii with Raney Nickel and heating can provide the compound of formula (I).

Scheme 13. Synthesis of the compound of formula (I)

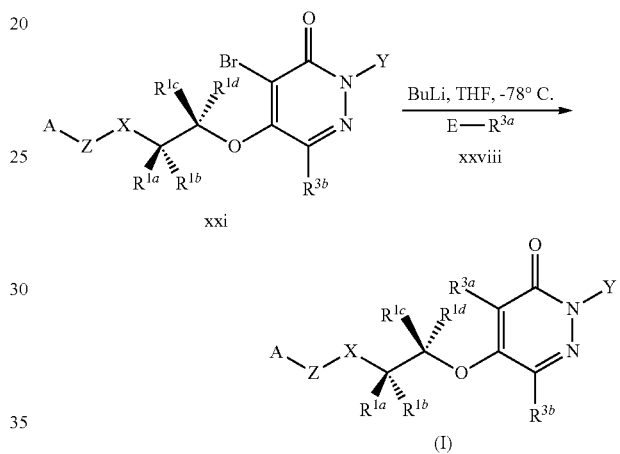

xxi (I)

The compound of formula (I) can be prepared from intermediate xxi (Scheme 13). The in situ generated organolithium intermediate of xxi can be treated with reagent xxviii, wherein E is any atom or group of atoms that renders R$^{3a}$, wherein R$^{3a}$ is as defined in the Summary of the Invention, suitably electrophilic for trapping the organolithium intermediate, to afford the compound of formula (I).

Scheme 14. Synthesis of the compound of formula (I)

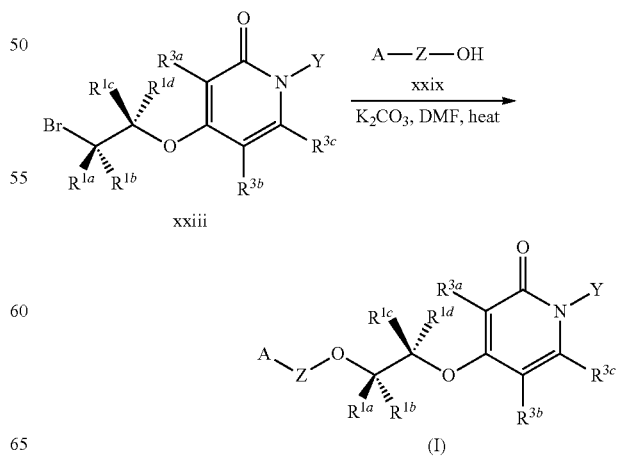

xxiii (I)

As illustrated in Scheme 14, the compound of formula (I) can be prepared from intermediate xxiii. The coupling of intermediate xxiii with alcohol xxix, wherein A and Z are as defined in the Summary of the Invention, can afford the compound of formula (I).

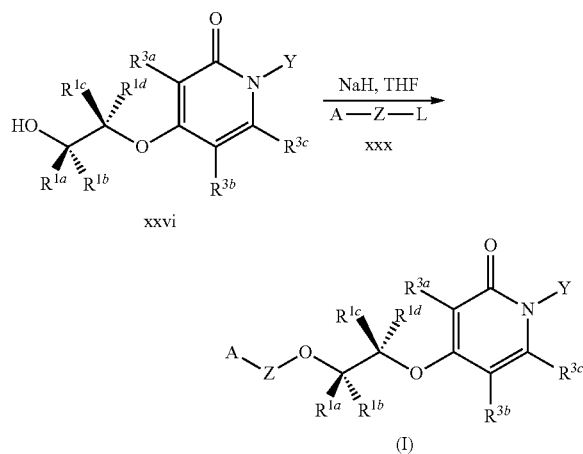

Scheme 15. Synthesis of the compound of formula (I)

As illustrated in Scheme 15, the compound of formula (I) can be prepared from intermediate xxvi. Reaction of intermediate xxvi with sodium hydride affords the corresponding alkoxide, which can undergo a nucleophilic aromatic substitution reaction with starting material xxx, wherein L is F, Cl, or Br and wherein A and Z are as defined in the Summary of the Invention, to provide the compound of formula (I).

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. PHARMACEUTICAL COMPOSITIONS

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *theobroma*. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., compound of formula (I)] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound [e.g., a compound of formula (I)], and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound [e.g., a compound of formula (I)], and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. METHODS OF TREATMENT

The disclosed compounds and compositions may be used in methods for treatment of $mGlu_3$ related medical disorders and/or diseases. The methods of treatment may comprise administering to a subject in need of such treatment a composition comprising a therapeutically effective amount of the compound of formula (I).

The compositions can be administered to a subject in need thereof to modulate $mGlu_2$, for a variety of diverse biological processes. The present disclosure is directed to methods for administering the composition to inhibit $mGlu_3$, a GPCR that plays a role in synaptic plasticity, which directly effects cognitive function and memory, for example.

The compositions may be useful for treating and preventing certain diseases and disorders in humans and animals related to $mGlu_3$ dysfunction. Treatment or prevention of such diseases and disorders can be effected by modulating $mGlu_3$ in a subject, by administering a compound or composition of the invention, either alone or in combination with another active agent as part of a therapeutic regimen to a subject in need thereof.

The compositions may be useful for treating a disease or disorder associated with dysfunction of $mGlu_3$, wherein the disease or disorder is selected from at least one of depression, Alzheimer's disease, dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance induced anxiety disorder.

The compositions may also be useful for the treatment of a proliferative disease or disorder.

a. Depression

Antidepressant-like effects of the $mGlu_{2/3}$ receptor antagonists, MGS0039 and LY341495, were first demonstrated in the rat forced swim test (FST) and mouse tail-suspension test (TST) using normal animals (Chaki et al. *Neuropharmacology*, 2004, 46, 457-467). More recently, studies have attempted to evaluate the effects of these drugs in paradigms implicated in the etiology of human depression. MGS0039 exhibited antidepressant effects in the learned helplessness test where treatment with MGS0039 for 7 days significantly reduced the number of escape failures (Yoshimizu et al. *Psychopharmacology*, 2006, 186, 587-593).

Palucha-Poniewiera et al. *Psychopharmacology*, 2010, 212, 523-535 evaluated a potential antidepressant-like effect of MGS0039 in the olfactory bulbectomy (OB) model of depression in rats. A surgical lesion of the olfactory bulbs in animals is known to induce significant behavioral, physiological, endocrine and immune changes, many of which are qualitatively similar to those observed in depressive patients. Repeated administration of MGS0039 for 14 days attenuated the hyperactivity of olfactory bulbectomized rats in the open field test and attenuated the learning deficit in the passive avoidance test.

Kawasaki et al. *Neuropharmacology*, 2011, 60, 397-404 also examined the effect of MGS0039 on behaviors of social isolation-reared mice in the FST. Rearing rodents in isolation after weaning is known to lead to changes in brain neurochemistry that produce perturbations in behavior. Post-weaning chronic social isolation for more than 6 weeks increased immobility in the FST, suggesting that isolation rearing caused depression-like behavior. MGS0039 reversed the increased immobility of social isolation reared mice in the test.

Campo, B. et al. *J. Neurogenetics* 2011, 25, 152-166, demonstrated a selective group II ($mGlu_2$ and $mGlu_3$) negative allosteric modulator (RO4491533) to be effective in several in vitro biochemical assays and in vivo models of depression. RO4491533 was shown to engage the central $mGlu_2$ and $mGlu_3$ receptors as the compound reversed the hypolocomotor effect of an $mGlu_{2/3}$ agonist (LY379268) in a target-specific manner. The known group II $mGlu_{2/3}$ antagonist LY341495 achieved the same result. RO4491533 and LY341495 dose-dependently reduced immobility time of C57Bl6/J mice in the FST. RO4491533 and LY341495 were also active in the tail suspension test in a line of Helpless (H) mice, a putative genetic model of depression.

Blockade of $mGlu_{2/3}$ receptors and ketamine may converge to the same neuronal circuits, which include activation of AMPA receptor and mTOR signaling. Because both AMPA receptor stimulation and subsequent mTOR signaling activation are presumed to be involved in rapid action of ketamine for patients with treatment-resistant depression (TRD), $mGlu_{2/3}$ receptor antagonists could exert the same effects in humans. This assumption is underpinned by several animal studies. First, the mGlu$_{2/3}$ receptor antagonist MGS0039 exhibited antidepressant effects in an animal model (the learned helplessness paradigm) which is refractory to currently prescribed antidepressants (Yoshimizu et al. *Psychopharmacology*, 2006, 186, 587-593). Second, although evidence of rapid onset of action with mGlu$_{2/3}$ receptor antagonists are absent, an AMPA receptor potentiator (AMPA receptor potentiation mediates antidepressant effects of mGlu$_{2/3}$ receptor antagonists) showed faster effects (during the first week of treatment) compared to fluoxetine (after two weeks) in a dominant-submissive test (Knapp et al. *Eur. J. Pharmacol.* 2002, 440, 121-125). Moreover, LY341495 exhibited a potent antidepressant effect in helpless mice following acute administration, while fluoxetine exerts a full antidepressant effect following chronic (21 days) treatment (Campo, B. et al. *J. Neurogenetics* 2011, 25, 152-166; El Yacoubi et al. *PNAS*, 2003, 100, 6227-6232). Therefore, blockade of mGlu$_3$ receptors may show rapid and potent antidepressant effects in humans.

b. Cognitive Disorders

Woltering et al. *Bioorg. Med. Chem. Lett.* 2010, 20, 6969-74, demonstrated that a negative allosteric modulator of mGlu$_{2/3}$ reversed mGlu$_{2/3}$ agonist or scopolamine-induced working memory deficits in the delayed match to position (DMTP) task in rodents, a measure of working memory. Additionally, Woltering demonstrated a synergistic reversal of scopolamine-induced deficits in DMTP when low doses of a negative allosteric modulator of mGlu$_{2/3}$ were combined with a threshold dose of the acetylcholinesterase inhibitor donezepil. Given the efficacy of donepezil and other acetylcholinesterase inhibitors in the treatment of the cognitive impairments in Alzheimer's disease, negative allosteric modulators of mGlu$_3$ may have efficacy as cognitive enhancers.

c. Obsessive-Compulsive Disorder

Shimazaki, T. et al. *Eur. J. Pharmacol.* 2004, 501, 121-125, demonstrated that MGS0039 induced glutamatergic change in mice, resulting in anti-obsessive-compulsive disorder activity. In these studies, a marble-burying behavioral test was utilized as a model for obsessive-compulsive disorder. The marble-burying behavior test is recognized as a useful model for evaluating the clinical potential of anti-obsessive-compulsive disorder drugs. Specifically, MGS0039 treated mice exhibited reduced marble-burying behavior in a significant and dose dependent manner, while no significant change was observed in spontaneous locomotor activity. In addition, LY341495, another potent antagonist of group II mGlu receptors, was also shown to significantly reduce marble-burying behavior in treated mice.

d. Alzheimer's Disease

Kim, S. H. et al. *Molecular Psychiatry* 2014, 1-8, have assessed the therapeutic potential of chronic pharmacological inhibition of group II mGlu receptors (mGlu$_2$ and mGlu$_3$) with a group II mGlu receptor antagonist in an APP transgenic mouse model that develops impaired learning behavior in relation to accumulation of mutant Aβ oligomers that never form amyloid plaques. Once-daily dosing of the orally bioavailable prodrug, BCI-838, delivered a sufficient brain concentration of its active metabolite BCI-632 to inhibit group II mGlu receptors for 22 hours. Three months of treatment with BCI-838 provided anxiolytic effects, reversed Dutch APP transgene-associated learning and memory impairment, and decreased the levels of monomeric and oAβ peptides in the hippocampus and cortex of the two different AD mouse models. Notably, BCI-838 administration stimulated hippocampal progenitor cell proliferation in both wild-type and Alzheimer's diseased mice for 3 months, which resulted in significantly increased numbers of newborn neurons in the hippocampi of Dutch APP transgenic mice. In addition to treatment, the proneurogenic properties make the compound attractive for potential use in reversing some of the early symptoms of Alzheimer's disease (AD), possibly through reparative effects of the newborn neurons. These findings suggest that chronic pharmacological inhibition of group II mGlu receptors has the potential to be a disease-modifying treatment for AD that targets cognitive/emotional defects and modulates neurogenesis.

Additional studies by Caraci, F. et al *Mol. Pharmacol.* 2011, 79, 618-626, showed that a positive allosteric modulator of mGlu$_2$ (LY566332) amplified Aβ-induced neurodegeneration, but this effect was prevented by the mGlu$_{2/3}$ receptor antagonist, LY341495.

e. Anxiety

Yoshimizu et al. *Psychopharmacology*, 2006, 186, 587-593 also demonstrated the anxiolytic effects of MGS0039, a potent antagonist of group II mGlu receptors (mGlu$_2$ and mGlu$_3$), by use of a conditioned fear stress (CFS) model, which represents emotional abnormality, including anxiety. The CFS model reflects psychological stress without physical stimuli, and is useful in predicting the clinical efficacy of anxiolytic drugs. In these studies, MGS0039 significantly decreased freezing behavior, as did diazepam and fluvoxamine, indicating the anxiolytic-like potential of MGS0039. The mGlu$_{2/3}$ receptors inhibit neurotransmitter release as autoreceptors located on glutamatergic terminals and treatment with mGlu$_{2/3}$' antagonists such as MGS0039 in vivo lead to an increase in extracellular glutamate. Therefore, the moderate elevation of glutamate levels in specific areas of the brain by MGS0039 may cause the anxiolytic-like effects seen in the CFS model. These results suggest that the blockade of mGlu$_3$ may be effective in the treatment of anxiety disorders.

f. Schizophrenia

Numerous studies have implicated glutamate neurotransmission, specifically aberrant N-methyl-D-aspartate receptor (NMDA) receptor function, as a key element in the pathophysiology of the schizophrenia (Kim J. et al. *Neurosci. Lett.* 1980, 20, 379-382.; Javitt, D. C; Zukin, S. R. *Am. J. Psychiatry* 1991, 148, 1301-1308.; Harrison, P. J.; Owen, M. J. *Lancet* 2003, 361, 417-419). According to this glutamate hypothesis of schizophrenia, a drug that can correct or modulate dysfunctional glutamatergic neurotransmission may be an effective therapeutic agent for schizophrenia The ability of mGlu$_3$ modulators to treat schizophrenia is demonstrated by Patil, S. et al. *Nature Medicine* 2007, 13, 1102-1107. Patil and coworkers report that LY404039 (an mGlu$_{2/3}$ modulator) was evaluated in schizophrenic patients in a randomized, three-armed, double-blind, placebo-controlled study. Treated patients showed statistically significant improvements in both positive and negative symptoms of schizophrenia compared to placebo (P<0.001 at week 4). These results suggest that modulators of mGlu$_3$ can have antipsychotic properties and can be used for the treatment of schizophrenia.

g. Cancer

Inhibition of mGlu$_3$ can lead to treatment and reduction of cancer or tumor growth, and/or reduce metastasis of cancerous or tumor cells. Accordingly, the disclosed compositions can be used in methods that treat and/or prevent cancer or tumors in a subject administered the composition. The method can treat cancer or tumor based growth and can be any type of cancer such as, but not limited to, glioma, melanoma, blood cancers (e.g., leukemia, lymphoma, myeloma, B cell acute lymphoblastic leukemia, hepatocellular carcinoma, B cell chronic lymphocytic lymphoma), lung carcinomas, esophageal squamous cell carcinomas, bladder cancer, colorectal cancer, esophageal cancer, gastric cancer, hepatocarcinoma, head and neck cancer, brain cancer, anal cancer, non-small cell lung carcinoma, pancreatic cancer, synovial carcinoma, prostate cancer, testicular cancer, liver cancer, cervical cancer, recurrent respiratory papillomatosis, skin cancer, multiple myeloma, astrocytoma, and stomach cancer, or any combination thereof.

In some embodiments, the administered composition to a subject in need thereof can mediate reduction, clearance or prevention of additional growth of tumor cells by inhibiting $mGlu_3$, thereby reducing growth/proliferation of tumor cells, but does not have an effect on normal cells.

In some embodiments, the administered composition can increase tumor free survival, reduce tumor mass, slow tumor growth, increase tumor survival, or a combination thereof in the subject. The administered composition can reduce tumor volume in the subject in need thereof. The administered composition can increase tumor free survival in the subject after administration of the composition.

In some embodiments, the composition can be administered to clear or eliminate the cancer or tumor expressing the one or more oncogenes without damaging or causing illness or death in the subject administered the composition.

Zhou et al. *Cell Biol. Int.* 2014, 38, 426-434, characterized, using both in vivo and in vitro methods, the effects of an $mGlu_3$ antagonist (LY341495) on the proliferation and differentiation of glioma stem cells (GSC). In vitro studies showed that the proliferation rates and proportion of cells in S phase within the LY341495 treated group decreased in a time-dependent manner. The growth rate and volume of tumors injected into nude mice was reduced in LY341495 treated mice compared with controls. Thus pharmacological blockade of $mGlu_3$ receptor signaling pathway significantly inhibits the growth and proliferation of GSCs both in vitro and in vivo while promoting differentiation to astrocytes. These results further implicate $mGlu_3$ in the biology of glioma and distinguish it as a cancer target.

h. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

i. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula (I). The above combinations include combinations of a compound of the present invention not only with one other active compound, but also with two or more other active compounds. For example, the compound of formula (I) can be combined with a variety of antidepressants, Alzheimer's disease medications, and anxiolytics.

The compound of formula (I) can be combined with the following antidepressants, but not limited to: Selective serotonin reuptake inhibitors (SSRIs) such as citalopram, dapoxetine, escitalopram, fluoxetine, fluvoxamine, indalpine, paroxetine, sertraline, and zimelidine; Serotonin-norepinephrine reuptake inhibitors (SNRIs) such as venlafaxine, desvenlafaxine, duloxetine, milnacipran, levomilnacipran, and sibutramine; Noradrenergic and specific serotonergic antidepressants (NaSSAs) or tetracyclic antidepressants (TeCAs) such as aptazapine, esmirtazapine, mianserin, mirtazapine, and setiptiline; Serotonin antagonist and reuptake inhibitors (SARIs) such as etoperidone, lorpiprazole, mepiprazole, nefazodone, trazodone, vilazodone, and niaprazine; Norepinephrine-dopamine reuptake inhibitors (NDRIs) such as armodafinil, bupropion, desoxypipradrol, dexmethylphenidate, methylphenidate, modafinil, prolintane, and tametraline; Serotonin-norepinephrine-dopamine reuptake inhibitors (SNDRIs) such as nefopam, amitifadine, tesofensine, and tedatioxetine; Tricyclic antidepressants (TCAs) such as clomipramine, desipramine, imipramine, dibenzepin, lofepramine, nortriptyline, protriptyline, amitriptyline, amitriptylinoxide, amoxapine, butriptyline, demexiptiline, dimetacrine, dosulepin, doxepin, imipraminoxide, melitracen, metapramine, nitroxazepine, noxiptiline, pipofezine, propizepine, quinupramine, aminoeptine, iprindole, opipramol, tianeptine, and trimipramine; and Negative allosteric modulators of metabotropic glutamate receptor 5 (mGlus) such as mavoglurant, basimglurant, dipraglurant, STX107, and N-(5-fluoropyridin-2-yl)-6-methyl-4-(pyrimidin-5-yloxy)picolinamide.

The compound of formula (I) can be combined with the following Alzheimer's disease medications, but not limited to: Acetylcholinesterase inhibitors such as tacrine, rivastigmine, galantamine, donepezil, edrophonium, physostigmine, pyridostigmine, ambenonium, rivastigmine, ladostigil, and ungeremine; and NMDA receptor antagonists such as memantine, amantadine, delucemine, and ketamine.

The compound of formula (I) can be combined with the following anxiolytics, but not limited to: buspirone, tandosprione, gepirone, adaptol, afobazole, hyroxyzine, validol, melatonin, and benzodiazepines such as alprazolam, chlordiazepoxide, clonazepam, diazepam, etizolam, lorazepam, oxazepam, and tofisopam.

The compound of formula (I) can be combined with the following chemotherapeutics or anti-cancer drugs, but not limited to: DNA alkylating agents such as temozolomide, cisplatin, carboplatin, nedaplatin, oxaliplatin, satraplatin, triplatin tetranitrate, procarbazine, altretamine, dacarbazine, and mitozolomide; and kinase inhibitors such as bevacizumab, enzastaurin, gefitinib, erlotinib, temsirolimus, everolimus, cilengitide, lapatinib, sunitinib, sorafenib, axitinib, pazopanib, vemurafenib, dabrafenib, and alisertib.

The disclosed compounds may be included in kits comprising the compound [e.g., one or more compounds of formula (I)], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

5. EXAMPLES

Examples 1-7 below give representative experimental procedures for the syntheses of intermediates useful for the synthesis of compounds of formula (I). Examples 8-15 give representative experimental procedures for completion of the syntheses of compounds of formula (I). Example 16 reports the biological activity of compounds of formula (I).

All NMR spectra were recorded on a 400 MHz AMX Bruker NMR spectrometer. $^1$H chemical shifts are reported in δ values in ppm downfield with the deuterated solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, integration. Reversed-phase LCMS analysis was performed using an Agilent 1200 system comprised of a binary pump with degasser, high-performance autosampler, thermostatted column compartment, C18 column, diode-array detector (DAD) and an Agilent 6150 MSD with the following parameters. The gradient conditions were 5% to 95% acetonitrile with the aqueous phase 0.1% TFA in water over 1.4 minutes. Samples were separated on a Waters Acquity UPLC BEH C18 column (1.7 μm, 1.0×50 mm) at 0.5 mL/min, with column and solvent temperatures maintained at 55° C. The DAD was set to scan from 190 to 300 nm, and the signals used were 220 nm and 254 nm (both with a band width of 4 nm). The MS detector was configured with an electrospray ionization source, and the low-resolution mass spectra were acquired by scanning from 140 to 700 AMU with a step size of 0.2 AMU at 0.13 cycles/second, and peak width of 0.008 minutes. The drying gas flow was set to 13 liters per minute at 300° C. and the nebulizer pressure was set to 30 psi. The capillary needle voltage was set at 3000 V, and the fragmentor voltage was set at 100V. Data acquisition was performed with Agilent Chemstation and Analytical Studio Reviewer software.

Example 1. 1-(4-Fluorophenyl)-4-hydroxypyridin-2 (1H)-one (D)

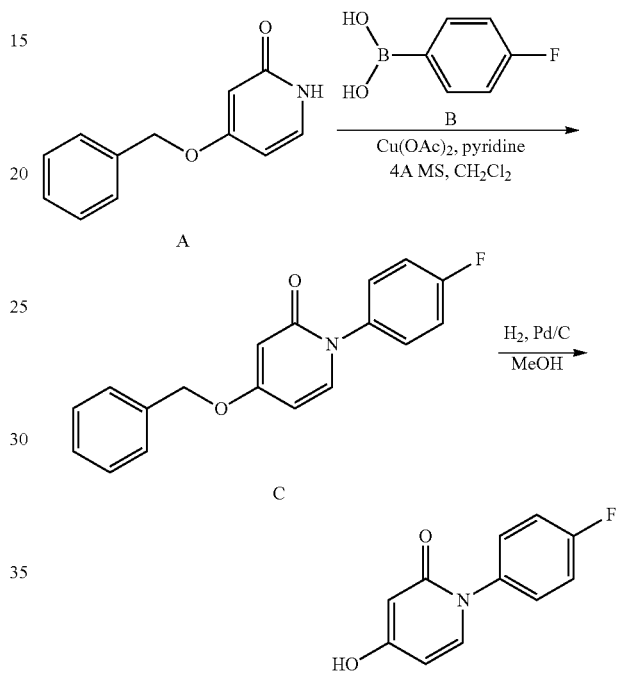

4-(Benzyloxy)-1-(4-fluorophenyl)pyridin-2(1H)-one (C)

A mixture of 4-(benzyloxy)pyridin-2(1H)-one (A) (1.00 g, 4.97 mmol, 1.0 eq.), 4-fluorophenylboronic acid (B) (1.39 g, 9.94 mmol, 2.0 eq.), pyridine (844 μL, 10.4 mmol, 2.1 eq.), copper (II) acetate (181 mg, 0.997 mmol, 0.20 eq.), and activated 4 Å molecular sieves in DCM (5 mL) was stirred for 100 hours at room temperature open to air. The reaction was poured into saturated sodium bicarbonate. The organic layer was separated, dried over magnesium sulfate, filtered and concentrated in vacuo. Purification by flash chromatography on silica gel using 0-70% hexanes/ethyl acetate afforded 1.05 g (72%) of the title compound. $^1$H NMR (400 MHz, DMSO-d$_6$) δ 7.58 (d, J=7.64 Hz, 1H), 7.48-7.3 (m, 9H), 6.11 (q, J=7.64, 2.7 Hz, 1H), 5.98 (d, J=2.64 Hz, 1H), 5.14 (s, 2H). ES-MS [M+1]$^+$: 296.4.

1-(4-Fluorophenyl)-4-hydroxypyridin-2(1H)-one (D)

To a solution of intermediate C (1.05 g, 3.56 mmol, 1.0 eq.) in methanol (25 mL) was added 10% palladium on carbon (200 mg) under nitrogen gas. After stirring for 18 hours under an atmosphere of hydrogen (balloon), the reaction was filtered through Celite®, washed with a 5% MeOH in DCM solution, and concentrated in vacuo to give 720 mg (99%) of the title compound, which was used without further purification. ES-MS [M+1]$^+$: 206.4.

Example 2. 4-(2-Phenoxyethoxy)pyridin-2(1H)-one (H)

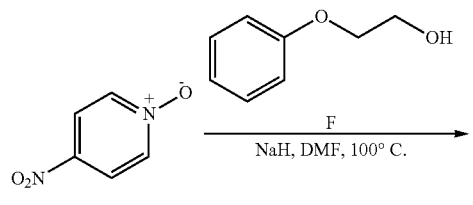

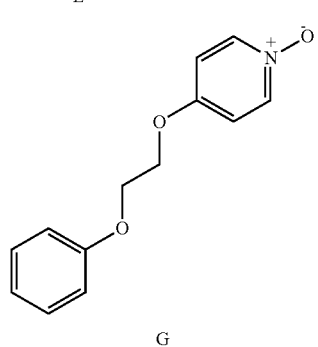

G

1-Oxido-4-(2-phenoxyethoxy)pyridin-1-ium (G)

To a solution of 2-phenoxyethanol (F) (1.24 mL, 10.0 mmol, 1.0 eq) in THF (50 mL) was added a 60% dispersion of sodium hydride in mineral oil (440 mg, 11.0 mmol, 1.1 eq) at 0° C. The solution was allowed to warm to room temperature and stirred for 30 minutes before adding 4-nitropyridine N-oxide (E) (1.40 g, 10.0 mmol, 1.0 eq). The reaction was then heated to 100° C. overnight. The solvent was removed in vacuo, and the crude product was purified by flash chromatography on silica gel using 0-10% methanol in DCM to afford 1.87 g (81%) of the title compound. ES-MS [M+1]$^+$: 232.4.

4-(2-Phenoxyethoxy)-1H-pyridin-2-one (H)

Compound G (500 mg, 2.16 mmol, 1.0 eq.) in acetic anhydride (0.203 mL, 2.16 mmol, 1.0 eq) was heated to 140° C. in a microwave reactor for one hour. The reaction was cooled to room temperature, and 1N aq. LiOH (20.3 mL, 5.0 eq) was added. The mixture was heated to 50° C. with stirring until completion. The solvent was removed in vacuo, and the crude product was dissolved in water, acidified to pH 4-5, and extracted with DCM. The organics were concentrated in vacuo. Purification by flash chromatography on silica gel using 0-5% methanol in DCM yielded 283 mg (57%) of the title compound. $^1$H NMR (400 MHz, DMSO-d$_6$) δ 11.10 (s, 1H), 7.31 (dd, J=7.2, 1.4 Hz, 2H), 7.24 (d, J 3.6 Hz, 1H), 6.99-6.94 (m, 3H), 5.89 (dd, J=4.3, 1.2, 1H), 5.76 (d, J=1.2 Hz, 1H), 4.28 (s, 4H). ES-MS [M+1]$^+$: 232.4.

Example 3. 4-(2-Phenoxyethoxy)pyrimidin-2(1H)-one (K)

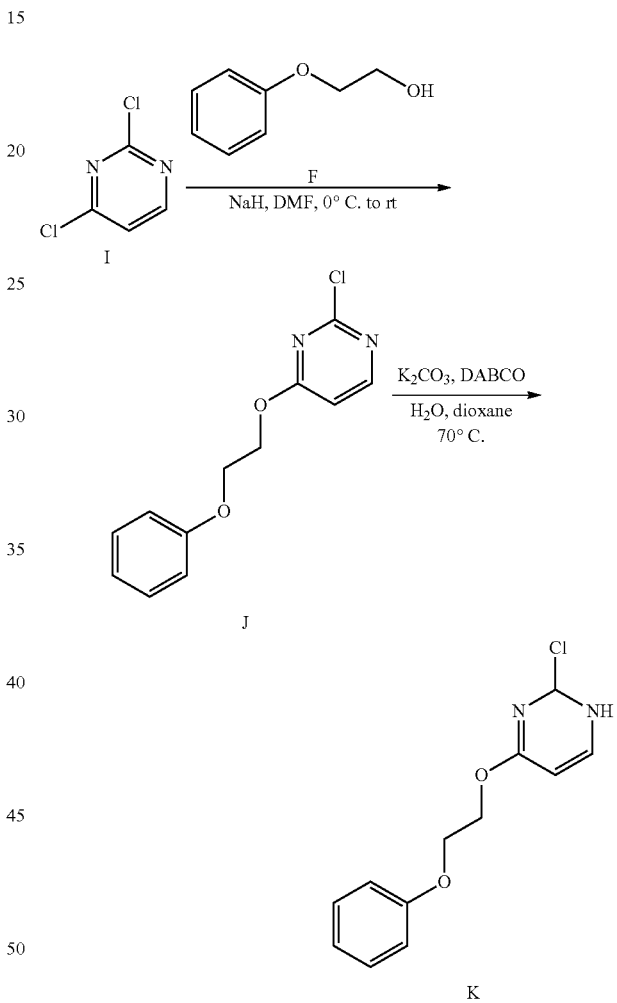

2-Chloro-4-(2-phenoxyethoxy)pyrimidine (J)

To a solution of 2-phenoxyethanol (F) (691 mg, 5.00 mmol, 1.0 eq.) in DMF (15.2 mL) at 0° C. was added a 60% dispersion of sodium hydride in mineral oil (600 mg, 15.0 mmol, 3.0 eq.) in several portions. After 10 min, 2,4-dichloropyrimidine (I) (745 mg, 5.00 mmol, 1.0 eq.) was added. The resulting mixture was stirred at 0° C. for 10 min and rt for 2 h. Saturated aq. NH$_4$Cl was added, and the mixture was diluted with ethyl acetate and water. The layers were separated, and the aqueous layer was extracted with ethyl acetate (3×). The combined organic extracts were washed with brine, dried over Na$_2$SO$_4$, filtered and concentrated in vacuo. Purification by flash chromatography on silica gel using 0-50% ethyl acetate/hexanes provided 500 mg (40%) of the title compound as a colorless oil. $^1$H NMR (400 MHz, DMSO-$d_6$) δ 8.49 (d, J=5.8 Hz, 1H), 7.32-7.28 (m, 2H), 7.07 (d, J=5.8 Hz, 1H), 6.98-6.94 (m, 3H), 4.69-4.466 (m, 2H), 4.34-4.32 (m, 2H). ES-MS [M+1]$^+$: 251.2.

4-(2-Phenoxyethoxy)pyrimidin-2(1H)-one (K)

A mixture of compound J (500 mg, 1.99 mmol, 1.0 eq.), potassium carbonate (497 mg, 3.59 mmol, 1.8 eq.) and 1,4-diazabicyclo[2.2.2]octane (0.11 mL, 1.0 mmol, 0.5 eq.) in 1,4-dioxane (20 mL) and water (20 mL) was stirred at 70° C. for 6 h. The reaction mixture was cooled to rt and solvents were removed in vacuo. The resulting residue was dissolved in water and extracted with DCM (3×). The combined organic extracts were washed with brine, dried over Na$_2$SO$_4$, filtered and concentrated in vacuo. Purification by flash chromatography on silica gel with 0-10% methanol/DCM afforded 383 mg (83%) of the title compound as a white solid. $^1$H NMR (400 MHz, DMSO-$d_6$) δ 11.36 (bs, 1H), 7.72 (d, J=7.0 Hz, 1H), 7.32-7.28 (m, 2H), 6.98-6.93 (m, 3H), 5.92 (d, J=7.0 Hz, 1H), 4.56-4.54 (m, 2H), 4.29-4.27 (m, 2H). ES-MS [M+1]$^+$: 233.4.

Example 4. 3-(4-Fluorophenyl)-2-(methylthio)-6-(2-phenoxyethoxy)pyrimidin-4(3H)-one (O)

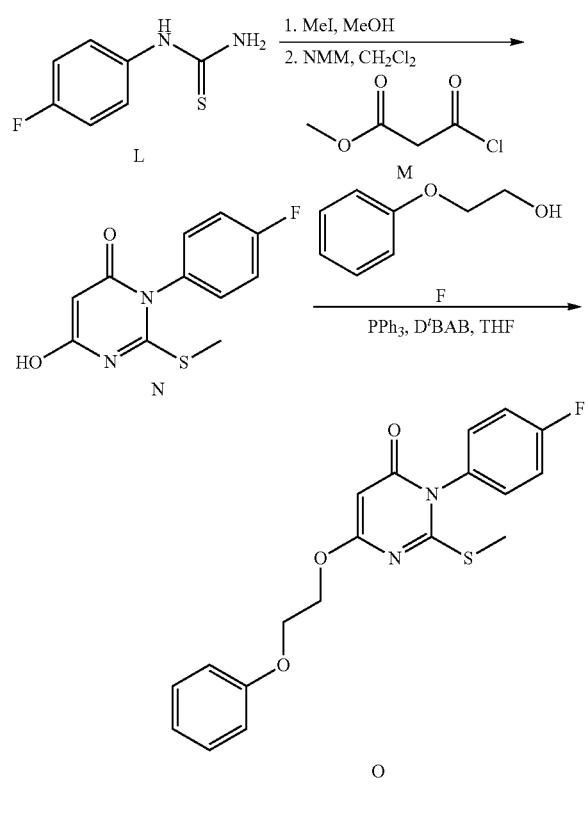

3-(4-fluorophenyl)-6-hydroxy-2-(methylthio)pyrimidin-4(3H)-one (N)

To a suspension of 1-(4-fluorophenyl)-2-thiourea (L) (2.30 g, 13.5 mmol, 1.0 eq.) in methanol (30 mL) at 0° C. was added iodomethane (1.01 mL, 16.2 mmol, 1.2 eq.). The mixture was stirred for 30 min at rt until a clear solution was obtained. Solvent was removed and the residue was dried in vacuo for 1 h. The residue was dissolved in DCM (50 mL), cooled to −5° C. and 4-methylmorpholine (2.97 mL, 27.0 mmol, 2.0 eq.) was added followed by the dropwise addition of methyl malonyl chloride (M) (2.17 mL, 20.2 mmol, 1.5 eq.). The resulting mixture was stirred at rt overnight under nitrogen. The mixture was cooled to −5° C. and additional amounts of 4-methylmorpholine (0.50 mL, 4.5 mmol, 0.33 eq.) and methyl malonyl chloride (0.50 mL, 4.7 mmol, 0.35 eq.) were added. The mixture was continued to stir at rt for 2 h and cooled to 10° C. Water (25 mL) and DCM (25 mL) were added. The mixture was stirred for 30 min. The interfacial solid was filtered, washed with water and dried in a vacuum oven to provide 557 mg (16%) of the title compound as a white solid. H NMR (400 MHz, DMSO-$d_6$) δ 11.95 (bs, 1H), 7.41-7.34 (m, 4H), 5.28 (s, 1H), 2.40 (s, 3H). ES-MS [M+1]$^+$: 253.2.

3-(4-fluorophenyl)-2-(methylthio)-6-(2-phenoxyethoxy)pyrimidin-4(3H)-one (O)

To a mixture of compound N (63.1 mg, 0.250 mmol, 1.0 eq.) and 2-phenoxyethanol (F) (37.4 μL, 0.300 mmol, 1.2 eq.) in THF (2.5 mL) at 0° C. was added triphenylphosphine (144 mg, 0.549 mmol, 2.2 eq.). The reaction mixture was stirred for 5 min and di-tert-butyl azodicarboxylate (92.1 mg, 0.400 mmol, 1.6 eq.) was added. The mixture was warmed to rt and stirred for 30 min. Solvent was removed. Purification using flash chromatography on silica gel with 0-70% ethyl acetate/hexanes afforded 67 mg (72%) of the title compound as a white crystalline solid. $^1$H NMR (400 MHz, DMSO-$d_6$) δ 7.46-7.37 (m, 4H), 7.34-7.39 (m, 2H), 7.00-6.94 (m, 3H), 5.58 (s, 1H), 4.59-4.57 (m, 2H), 4.33-4.31 (m, 2H), 2.43 (s, 3H). ES-MS [M+1]$^+$: 373.2.

Example 5. 4-Bromo-2-(4-fluorophenyl)-5-(2-phenoxyethoxy)pyridazin-3(2H)-one (S)

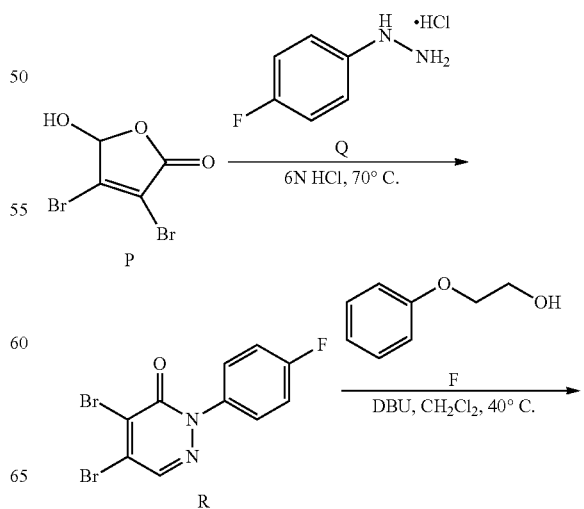

-continued

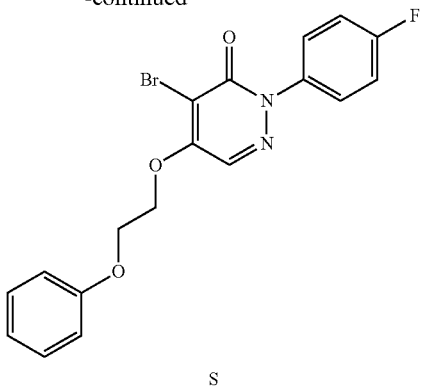

S 4,5-Dibromo-2-(4-fluorophenyl)pyridazin-3(2H)-one (R)

A solution of (4-fluorophenyl)hydrazine hydrochloride (Q) (3.90 g, 24.0 mmol, 1.2 eq.) in 6N aq. HCl (50 mL) was added to a suspension of 3,4-dibromo-2-hydroxy-2H-furan-5-one (P) (5.16 g, 20.0 mmol, 1.0 eq.) in 6N aq. HCl (100 mL). The reaction mixture was stirred vigorously at 70° C. overnight. The mixture was cooled and filtered. The precipitate was washed with diethyl ether and dried in a vacuum oven overnight. Purification using flash chromatography on silica gel with 10% MeOH/DCM afforded 1.36 g (20%) of the title compound as an off white powder. $^1$H NMR (400 MHz, DMSO-$d_6$) δ 8.28 (s, 1H), 7.63-7.58 (m, 2H), 7.39-7.33 (m, 2H). ES-MS [M+1]$^+$: 349.0.

4-Bromo-2-(4-fluorophenyl)-5-(2-phenoxyethoxy)pyridazin-3(2H)-one (S)

To a suspension of compound R (174 mg, 0.500 mmol, 1.0 eq.) in DCM (2.5 mL, 0.2 M) was added 2-phenoxyethanol (F) (74.8 μL, 0.596 mmol, 1.2 eq.) and 1,8-diazabicyclo[5.4.0]undec-7-ene (150 μL, 1.00 mmol, 2.0 eq.). The reaction mixture was stirred at rt for 18 h and heated to 40° C. for 30 min to increase solubility. The mixture was diluted with DCM and washed with 1N aq. HCl (2×), saturated aq. NaHCO$_3$ (2×) and brine. The organic layer was dried over anhydrous MgSO$_4$, filtered and concentrated in vacuo. Purification using flash chromatography on silica gel using 0-70% ethyl acetate/hexanes provide 67 mg (33%) of the title compound as a white crystalline solid. $^1$H NMR (400 MHz, DMSO-$d_6$) δ 8.38 (s, 1H), 7.59-7.56 (m, 2H), 7.37-7.29 (m, 4H), 7.00-6.96 (m, 3H), 4.81-4.79 (m, 2H), 4.38-4.36 (m, 2H). ES-MS [M+1]$^+$: 405.2.

Example 6. 4-(2-Bromoethoxy)-1-(4-fluorophenyl)pyridin-2(1H)-one (U)

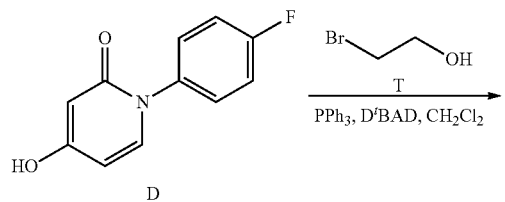

-continued

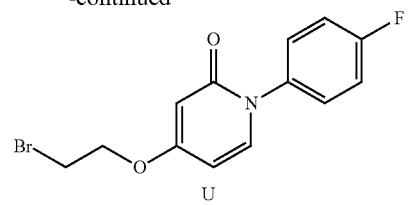

U 4-(2-Bromoethoxy)-1-(4-fluorophenyl)pyridin-2(1H)-one (U)

To a solution of compound D (100 mg, 0.487 mmol, 1.0 eq.) and 2-bromoethanol (T) (42 μL, 0.58 mmol, 1.2 eq.) in THF (3 mL) cooled to 0° C. was added triphenylphosphine (281 mg, 1.07 mmol, 2.2 eq.) and D$^t$BAD (180 mg, 0.782 mmol, 1.6 eq.). The reaction was concentrated to dryness after three hours of stirring. Purification by flash chromatography on silica gel using 0-60% hexanes/ethyl acetate afforded the title compound contaminated with triphenylphosphine oxide (quantitative yield was assumed in next reaction and impure material was carried forward). ES-MS [M+1]$^+$: 312.2.

Example 7. 1-(4-Fluorophenyl)-4-(2-hydroxyethoxy)pyridin-2(1H)-one (X)

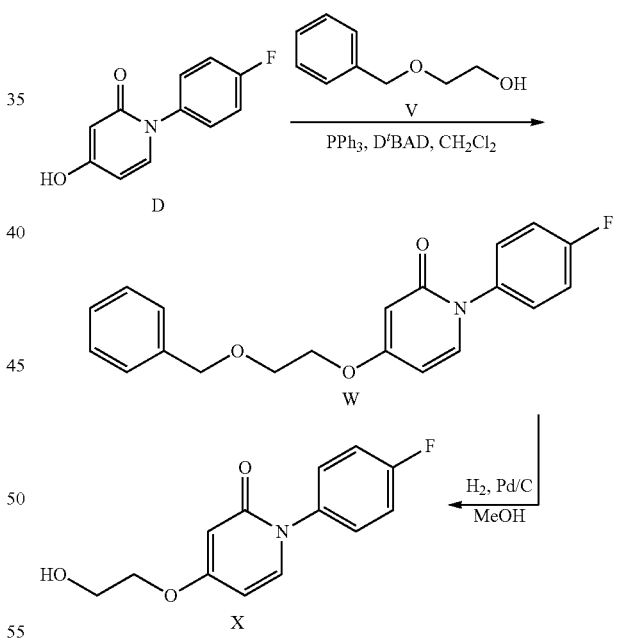

4-(2-(Benzyloxy)ethoxy)-1-(4-fluorophenyl)pyridin-2(1H)-one (W)

To a solution of compound D (200 mg, 0.975 mmol, 1.0 eq.) and 2-benzyloxyethanol (V) (166 μL, 1.17 mmol, 1.2 eq.) in THF (4.9 mL) cooled to 0° C. was added triphenylphosphine (562 mg, 2.14 mmol, 2.2 eq.) and D$^t$BAD (359 mg, 1.56 mmol, 1.6 eq.). The reaction was concentrated to dryness after two hours of stirring. Purification by flash chromatography on silica gel using 0-60% hexanes/ethyl acetate afforded 250 mg (76%) of the title compound. $^1$H NMR (400 MHz, DMSO-$d_6$) δ 7.56 (d, J=7.64 Hz, 1H), 7.43-7.3 (m, 9H), 6.08 (q, J=7.64, 2.7 Hz, 1H), 5.9 (d, J=2.7, 1H), 4.56 (s, 2H), 4.18 (m, 2H), 3.77 (m, 2H). ES-MS [M+1]$^+$: 340.2.

1-(4-Fluorophenyl)-4-(2-hydroxyethoxy)pyridin-2 (1H)-one (X)

To a solution of compound W (250 mg, 0.737 mmol, 1.0 eq.) in methanol (5 mL) was added 10% palladium on carbon (75 mg) under nitrogen gas. After stirring for 18 hours under an atmosphere of hydrogen (balloon), the reaction was filtered through Celite®, washed well with a 5% MeOH in DCM solution, and concentrated in vacuo. Purification by flash chromatography on silica gel using 0-10% MeOH/DCM afforded 160 mg (64%) of the title compound. $^1$H NMR (400 MHz, DMSO-$d_6$) δ 7.56 (d, J=7.64 Hz, 1H), 7.43-7.40 (m, 2H), 7.34-7.30 (m, 2H), 6.05 (dd, J=2.72, 7.64 Hz, 1H), 5.88 (d, J=2.64 Hz, 1H), 4.93 (t, J=5.28, 5.4 Hz, 1H), 4.01 (t, J=4.6, 4.92 Hz, 2H), 3.72 (q, J=4.96, 9.44 Hz, 2H). ES-MS [M+1]$^+$: 250.2.

Example 8. 1-(4-Fluorophenyl)-4-(2-phenoxypropoxy)pyridin-2(1H)-one (1)

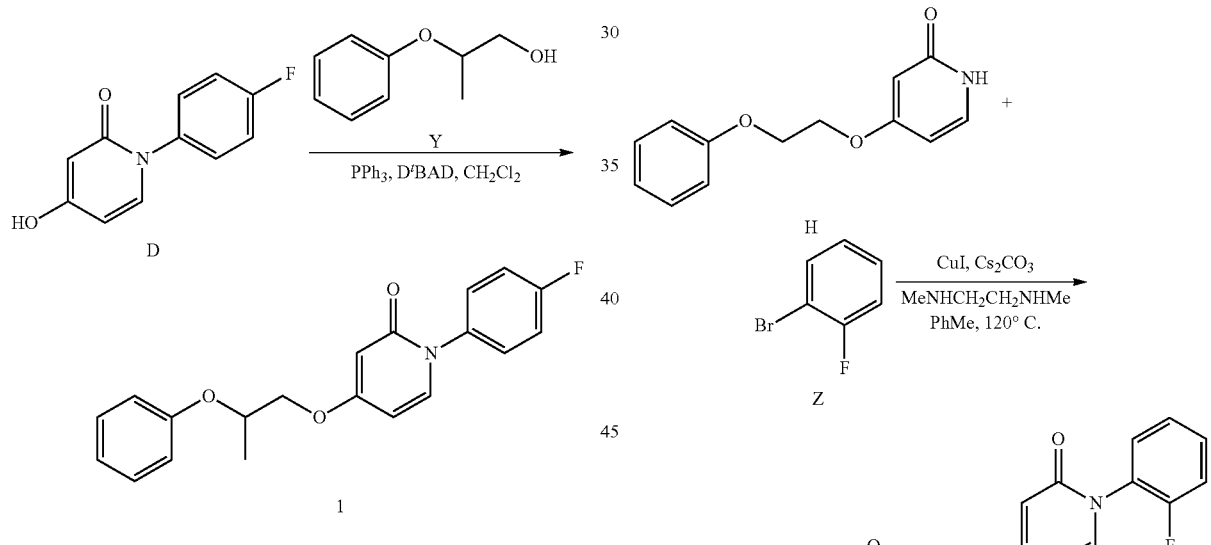

1-(4-Fluorophenyl)-4-(2-phenoxypropoxy)pyridin-2 (1H)-one (1): To a solution of compound D (10 mg, 0.049 mmol, 1.0 eq.) and 2-phenoxypropanol (Y) (8.3 μL, 0.059 mmol, 1.2 eq.) in THF (1 mL) cooled to 0° C. was added triphenylphosphine (28 mg, 0.11 mmol, 2.2 eq.) and D$^t$BAD (18 mg, 0.078 mmol, 1.6 eq.). The reaction was concentrated to dryness after 18 hours of stirring. Purification by reverse phase HPLC afforded 11.9 mg (72%) of the title compound. $^1$H NMR (400 MHz, DMSO-$d_6$) δ 7.54 (d, J=7.64 Hz, 1H), 7.41-7.38 (m, 2H), 7.32-7.26 (m, 4H), 6.98-6.91 (m, 3H), 6.03 (dd, J=2.72, 7.64 Hz, 1H), 5.92 (d, J=2.68 Hz, 1H), 4.84-4.80 (m, 1H), 4.19-4.11 (m, 2H), 1.32 (d, J=6.24 Hz, 3H). ES-MS [M+1]$^+$: 340.3.

The following compounds were prepared in an analogous manner by first preparing the appropriate synthetic intermediate by use of the synthetic procedures indicated next to each compound:

| No. | Name | Example used to prepare intermediate compound | ES-MS [M + 1]$^+$ |
|---|---|---|---|
| 2 | 1-(4-fluorophenyl)-4-(3-phenylpropoxy)pyridin-2(1H)-one | 1 | 324.2 |
| 3 | 1-(4-fluorophenyl)-4-(2-(phenylthio)ethoxy)pyridin-2(1H)-one | 1 | 342.2 |
| 4 | 1-(4-fluorophenyl)-4-(2-(methyl(phenyl)amino)ethoxy)pyridin-2(1H)-one | 1 | 339.2 |
| 5 | 1-(4-fluorophenyl)-4-((1-phenoxypropan-2-yl)oxy)pyridin-2(1H)-one | 1 | 340.3 |
| 6 | 4-(2-(cyclopentyloxy)ethoxy)-1-(4-fluorophenyl)pyridin-2(1H)-one | 1 | 318.3 |
| 7 | 4-(2-(cyclohexyloxy)ethoxy)-1-(4-fluorophenyl)pyridin-2(1H)-one | 1 | 332.4 |
| 8 | 1-(4-fluorophenyl)-4-(2-(phenylsulfinyl)ethoxy)pyridin-2(1H)-one | 1 | 358.2 |
| 9 | 1-(4-fluorophenyl)-4-(2-(phenylsulfonyl)ethoxy)pyridin-2(1H)-one | 1 | 374.2 |

Example 9. 1-(2-Fluorophenyl)-4-(2-phenoxyethoxy)pyridin-2-one (10)

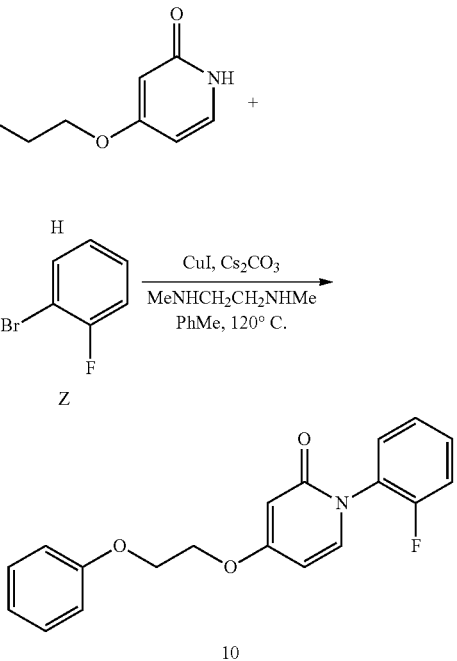

1-(2-Fluorophenyl)-4-(2-phenoxyethoxy)pyridin-2-one (10)

A vial was charged with compound H (15 mg, 0.065 mmol, 1.0 eq), 1-bromo-2-fluorobenzene (Z) (35 μL, 0.32 mmol, 5.0 eq), cesium carbonate (43 mg, 0.13 mmol, 2.0 eq), N,N'-dimethylethylenediamine (17.5 μL, 0.16 mmol, 2.5 eq), toluene (650 μL), and copper (I) iodide (12 mg, 0.065 mmol, 1.0 eq). The vial was flushed with nitrogen, capped, and heated to 120° C. for 12 hours. Once complete, the solvent was removed, and the crude product was purified by reverse phase HPLC to yield 2.4 mg (11%) of the title compound. $^1$H NMR (400 MHz, DMSO-$d_6$) δ 7.57-7.29 (m, 7H), 7.00-6.94 (m, 3H), 6.11 (dd, J 2.3, 1.3 Hz, 1H), 5.98 (d, J 1.3 Hz, 1H), 4.37-4.31 (m, 4H). ES-MS [M+1]$^+$: 326.4.

The following compounds were prepared in an analogous manner by first preparing the appropriate synthetic intermediate by use of the synthetic procedures indicated next to each compound:

| No. | Name | Example used to prepare intermediate compound | ES-MS [M + 1]$^+$ |
| --- | --- | --- | --- |
| 11 | 4-(2-phenoxyethoxy)-2H-[1,2'-bipyridin]-2-one | 2 | 309.2 |
| 12 | 6'-fluoro-4-(2-phenoxyethoxy)-2H-[1,2'-bipyridin]-2-one | 2 | 327.3 |
| 13 | 4-(2-phenoxyethoxy)-2H-[1,4'-bipyridin]-2-one | 2 | 309.4 |
| 14 | 1-(3-fluorophenyl)-4-(2-phenoxyethoxy)pyrimidin-2(1H)-one | 3 | 327.2 |
| 15 | 1-(3,4-difluorophenyl)-4-(2-phenoxyethoxy)pyrimidin-2(1H)-one | 3 | 345.2 |
| 16 | 1-(5-fluoropyridin-2-yl)-4-(2-phenoxyethoxy)pyrimidin-2(1H)-one | 3 | 328.2 |

Example 10. 1-(4-Fluorophenyl)-4-(2-phenoxyethoxy)pyrimidin-2(1H)-one (17)

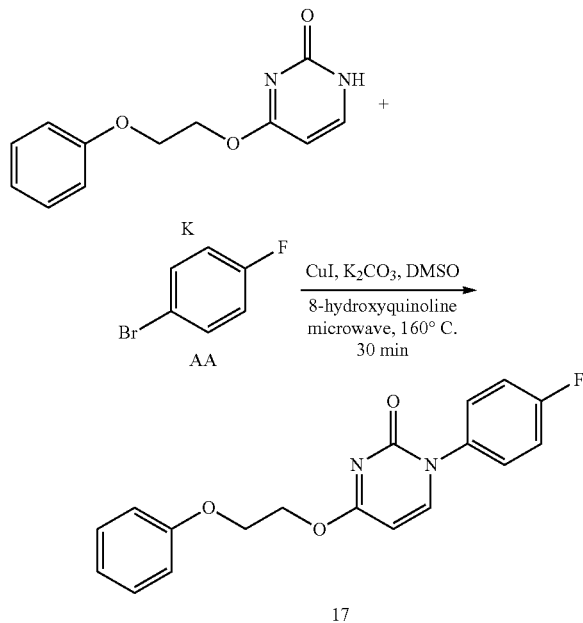

1-(4-Fluorophenyl)-4-(2-phenoxyethoxy)pyrimidin-2 (1H)-one (17)

A mixture of compound K (23.2 mg, 0.100 mmol, 1.0 eq.), 4-bromofluorobenzene (AA) (17.5 mg, 0.100 mmol, 1.0 eq.), copper (I) iodide (6.3 mg, 0.033 mmol, 0.33 eq.), potassium carbonate (20.7 mg, 0.150 mmol, 1.5 eq.) and 8-hydroxyquinoline (4.8 mg, 0.033 mmol, 0.33 eq.) in DMSO (0.83 mL) was heated in a microwave reactor at 160° C. for 30 min. The reaction mixture was cooled to rt and filtered using a syringe filter, and the solid was rinsed with DMSO (0.5 mL). Purification using reverse phase HPLC afforded 5.1 mg (16%) of the title compound as a white solid. $^1$H NMR (400 MHz, CDCl$_3$) δ 7.52 (d, J=7.2 Hz, 1H), 7.40-7.30 (m, 4H), 7.22-7.17 (m, 2H), 7.02-6.96 (m, 3H), 6.08 (d, J=7.2 Hz, 1H), 4.84-4.81 (m, 2H), 4.36-4.33 (m, 2H). ES-MS [M+1]$^+$: 233.4.

Example 11. 1-(4-Fluorophenyl)-4-(2-phenoxyethoxy)pyridin-2(1H)-one (18)

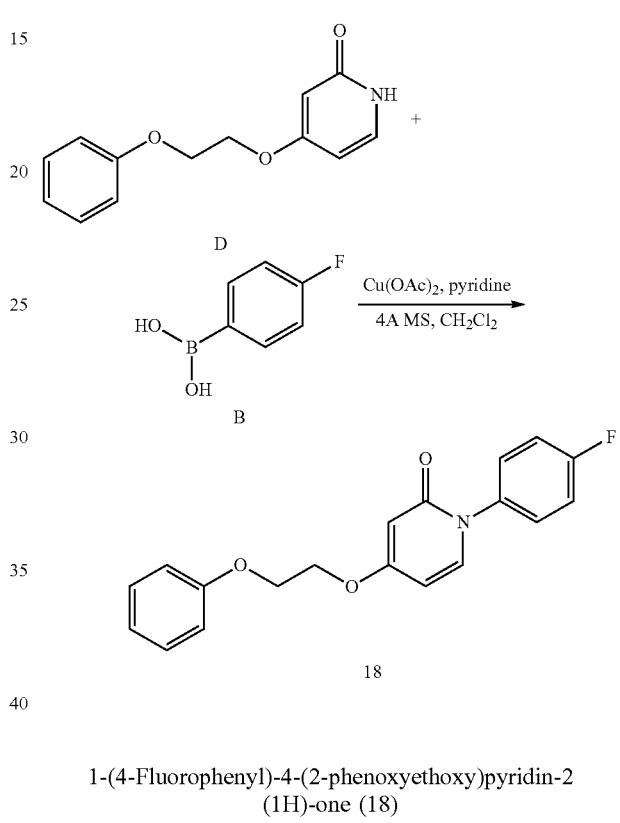

1-(4-Fluorophenyl)-4-(2-phenoxyethoxy)pyridin-2 (1H)-one (18)

A slurry of compound D (15 mg, 0.065 mmol, 1.0 eq), 4-fluorophenylboronic acid (B) (13 mg, 0.093 mmol, 1.4 eq), copper(II) acetate (2.4 mg, 0.013 mmol, 0.2 eq), pyridine (11 µL, 0.14 mmol, 2.1 eq), and 4 Å activated molecular sieves in dichloromethane (0.65 mL) was allowed to stir at room temperature while open to air for 12 hours. Upon completion, the crude product was poured into saturated NaHCO$_3$ and extracted with dichloromethane. The organics were concentrated in vacuo, and the crude product was purified by reverse phase HPLC to yield 6.9 mg (33%) of the title compound. $^1$H NMR (400 MHz, DMSO-$d_6$) δ 7.58 (d, J=7.64 Hz, 1H), 7.44-7.41 (m, 2H), 7.35-7.29 (m, 4H), 7.0-6.95 (m, 3H), 6.09 (dd, J=2.72, 7.64 Hz, 1H), 5.97 (d, J=2.68 Hz, 1H), 4.37-4.31 (m, 4H). ES-MS [M+H]$^+$: 326.3.

The following compounds were prepared in an analogous manner by first preparing the appropriate synthetic intermediate by use of the synthetic procedures indicated next to each compound:

| No. | Name | Example used to prepare intermediate compound | ES-MS [M + 1]+ |
|---|---|---|---|
| 19 | 1-(3-fluorophenyl)-4-(2-phenoxyethoxy)pyridin-2(1H)-one | 2 | 326.3 |
| 20 | 1-(3,4-difluorophenyl)-4-(2-phenoxyethoxy)pyridin-2(1H)-one | 2 | 344.3 |
| 21 | 1-(3,5-difluorophenyl)-4-(2-phenoxyethoxy)pyridin-2(1H)-one | 2 | 344.2 |
| 22 | 3-(2-oxo-4-(2-phenoxyethoxy)pyridin-1(2H)-yl)benzonitrile | 2 | 333.0 |
| 23 | 3-fluoro-5-(2-oxo-4-(2-phenoxyethoxy)pyridin-1(2H)-yl)benzonitrile | 2 | 351.2 |
| 24 | 4-(2-oxo-4-(2-phenoxyethoxy)pyridin-1(2H)-yl)benzonitrile | 2 | 333.3 |
| 25 | 6'-fluoro-4-(2-phenoxyethoxy)-2H-[1,3'-bipyridin]-2-one | 2 | 327.0 |
| 26 | 2-oxo-4-(2-phenoxyethoxy)-2H-[1,3'-bipyridine]-5'-carbonitrile | 2 | 334.2 |
| 27 | 5'-fluoro-4-(2-phenoxyethoxy)-2H-[1,3'-bipyridin]-2-one | 2 | 327.2 |

Example 12: 3-(4-Fluorophenyl)-6-(2-phenoxyethoxy)pyrimidin-4(3H)-one (28)

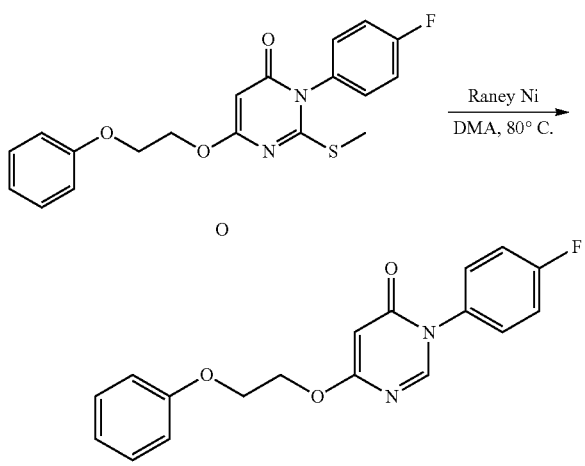

28

3-(4-Fluorophenyl)-6-(2-phenoxyethoxy)pyrimidin-4(3H)-one (28)

Compound O (37.2 mg, 0.100 mmol, 1.0 eq.) was dissolved in DMA (0.40 mL) and heated to 80° C. Raney-Nickel (~30 mg) was added. A slight exotherm and gas evolution were observed. The reaction mixture was stirred vigorously for 1 h. Additional Raney-Nickel was added until the reaction was judged complete. The reaction mixture was filtered through a pad of Celite, and the solid was rinsed with ethyl acetate. Purification using reverse phase HPLC afforded 8.2 mg (25%) of the title compound as a white solid. $^1$H NMR (400 MHz, DMSO-$d_6$) δ 8.43 (s, 1H), 7.54-7.51 (m, 2H), 7.42-7.36 (m, 2H), 7.33-7.29 (m, 2H), 7.00-6.91 (m, 3H), 5.80 (s, 1H), 4.57-4.52 (m, 2H), 4.40-4.30 (m, 2H). ES-MS [M+1]+: 327.3.

Example 13. 2-(4-Fluorophenyl)-5-(2-phenoxyethoxy)pyridazin-3(2H)-one (29)

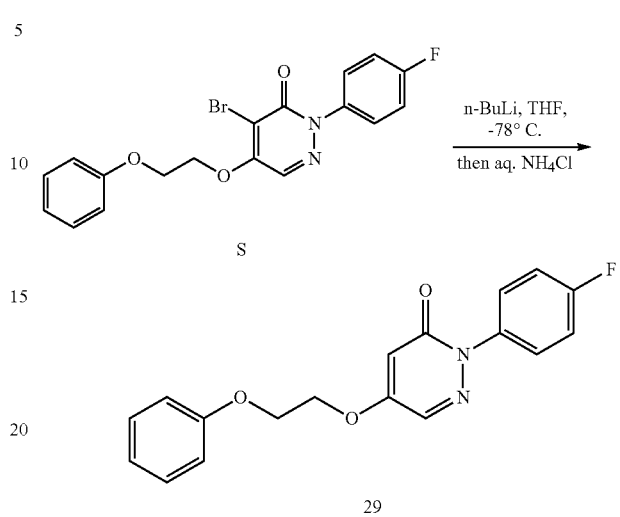

29

2-(4-Fluorophenyl)-5-(2-phenoxyethoxy)pyridazin-3(2H)-one (29)

To a solution of compound S (40.5 mg, 0.100 mmol, 1.0 eq.) in THF (0.5 mL, 0.2 M) at −78° C. was added n-butyllithium (1.6 M in hexanes, 75 μL, 0.12 mmol, 1.2 eq.). The reaction was stirred for 15 min at −78° C. Saturated aq. NH$_4$Cl was added. The mixture was warmed to rt and extracted with ethyl acetate (3×). The combined organic layers was dried over Na$_2$SO$_4$, filtered and concentrated in vacuo. Purification using reverse phase HPLC afforded 6.0 mg (18%) of the title compound as an off white solid. $^1$H NMR (400 MHz, DMSO-$d_6$) δ 7.98 (d, J=2.8 Hz, 1H), 7.56-7.53 (m, 2H), 7.34-7.30 (m, 4H), 7.00-6.96 (m, 3H), 6.53 (d, J=2.8 Hz, 1H), 4.47-4.45 (m, 2H), 4.36-4.34 (m, 2H). ES-MS [M+1]+: 327.2.

Example 14. 1-(4-Fluorophenyl)-4-(2-phenoxyethoxy)pyridin-2(1H)-one (18)

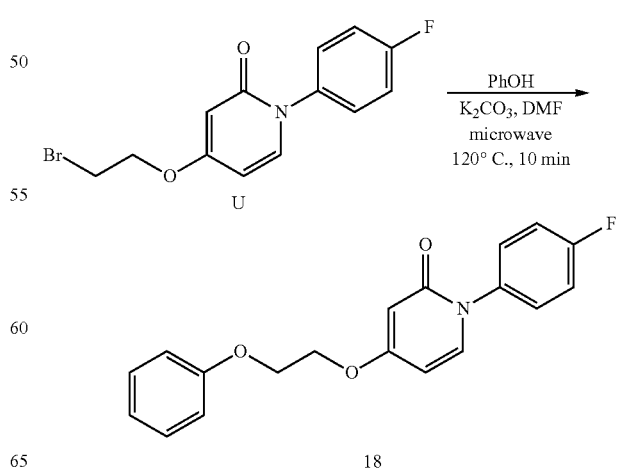

18

1-(4-Fluorophenyl)-4-(2-phenoxyethoxy)pyridin-2 (1H)-one (18)

Compound U (10 mg, 0.032 mmol, 1.0 eq.), phenol (3.6 mg, 0.038 mmol, 1.2 eq.), potassium carbonate (9.3 mg, 0.067 mmol, 2.1 eq.) and DMF (600 µL) were added to a small microwave vial. The vial was capped and heated in the microwave reactor at 120° C. for ten minutes. Purification by reverse phase HPLC afforded 5.6 mg (54%, 2 steps) of the title compound. $^1$H NMR (400 MHz, DMSO-$d_6$) δ 7.58 (d, J=7.64 Hz, 1H), 7.44-7.41 (m, 2H), 7.35-7.29 (m, 4H), 7.0-6.95 (m, 3H), 6.09 (dd, J=2.72, 7.64 Hz, 1H), 5.97 (d, J=2.68 Hz, 1H), 4.37-4.31 (m, 4H). ES-MS [M+1]$^+$: 326.2.

The following compounds were prepared in an analogous manner by first preparing the appropriate synthetic intermediate by use of the synthetic procedures indicated next to each compound:

Example 15. 4-(2-((4-Chloropyridin-2-yl)oxy)ethoxy)-1-(4-fluorophenyl)pyridin-2(1H)-one (49)

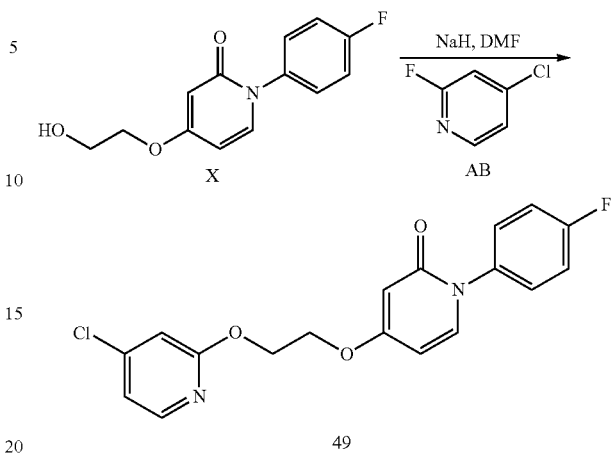

| No. | Name | Example used to prepare intermediate compound | ES-MS [M + 1]$^+$ |
|---|---|---|---|
| 30 | 4-(2-(2-fluorophenoxy)ethoxy)-1-(4-fluorophenyl)pyridin-2(1H)-one | 1, 6 | 344.3 |
| 31 | 4-(2-(3-fluorophenoxy)ethoxy)-1-(4-fluorophenyl)pyridin-2(1H)-one | 1, 6 | 344.2 |
| 32 | 4-(2-(4-fluorophenoxy)ethoxy)-1-(4-fluorophenyl)pyridin-2(1H)-one | 1, 6 | 344.2 |
| 33 | 4-(2-(2,3-difluorophenoxy)ethoxy)-1-(4-fluorophenyl)pyridin-2(1H)-one | 1, 6 | 362.3 |
| 34 | 4-(2-(2,4-difluorophenoxy)ethoxy)-1-(4-fluorophenyl)pyridin-2(1H)-one | 1, 6 | 362.2 |
| 35 | 4-(2-(2,5-difluorophenoxy)ethoxy)-1-(4-fluorophenyl)pyridin-2(1H)-one | 1, 6 | 362.3 |
| 36 | 4-(2-(2,6-difluorophenoxy)ethoxy)-1-(4-fluorophenyl)pyridin-2(1H)-one | 1, 6 | 362.2 |
| 37 | 4-(2-(2-chlorophenoxy)ethoxy)-1-(4-fluorophenyl)pyridin-2(1H)-one | 1, 6 | 360.2 |
| 38 | 4-(2-(3-chlorophenoxy)ethoxy)-1-(4-fluorophenyl)pyridin-2(1H)-one | 1, 6 | 360.2 |
| 39 | 4-(2-(4-chlorophenoxy)ethoxy)-1-(4-fluorophenyl)pyridin-2(1H)-one | 1, 6 | 360.2 |
| 40 | 1-(4-fluorophenyl)-4-(2-((2-fluoropyridin-3-yl)oxy)ethoxy)pyridin-2(1H)-one | 1, 6 | 345.2 |
| 41 | 3-(2-((1-(4-fluorophenyl)-2-oxo-1,2-dihydropyridin-4-yl)oxy)ethoxy)benzonitrile | 1, 6 | 351.2 |
| 42 | 4-(2-((1-(4-fluorophenyl)-2-oxo-1,2-dihydropyridin-4-yl)oxy)ethoxy)benzonitrile | 1, 6 | 351.2 |
| 43 | 1-(4-fluorophenyl)-4-(2-(4-(methoxymethyl)phenoxy)ethoxy)pyridin-2(1H)-one | 1, 6 | 370.2 |
| 44 | 1-(4-fluorophenyl)-4-(2-(pyridin-3-yloxy)ethoxy)pyridin-2(1H)-one | 1, 6 | 327.2 |
| 45 | 1-(4-fluorophenyl)-4-(2-((6-fluoropyridin-3-yl)oxy)ethoxy)pyridin-2(1H)-one | 1, 6 | 345.2 |
| 46 | 4-(2-((5-chloropyridin-3-yl)oxy)ethoxy)-1-(4-fluorophenyl)pyridin-2(1H)-one | 1, 6 | 361.2 |
| 47 | 4-(2-((4-chloropyridin-3-yl)oxy)ethoxy)-1-(4-fluorophenyl)pyridin-2(1H)-one | 1, 6 | 361.2 |
| 48 | 4-(2-((2-chloropyridin-3-yl)oxy)ethoxy)-1-(4-fluorophenyl)pyridin-2(1H)-one | 1, 6 | 361.2 |

4-(2-((4-Chloropyridin-2-yl)oxy)ethoxy)-1-(4-fluorophenyl)pyridin-2(1H)-one (49)

To a solution of 4-chloro-2-fluoropyridine (AB) (9.1 µL, 0.092 mmol, 2.0 eq.) and a 60 dispersion of sodium hydride in mineral oil (2.3 mg, 0.092 mmol, 2.0 eq.) in DMF (1 mL) was added compound X (11.5 mg, 0.0461 mmol, 1.0 eq.). After 18 hours, the reaction was diluted with ethyl acetate and washed with water and brine twice. The organics were combined, dried over magnesium sulfate, filtered, and concentrated in vacuo. Purification by reverse phase HPLC afforded 14.5 mg (87%) of the title compound. $^1$H NMR (400 MHz, DMSO-$d_6$) δ 8.19 (d, J=5.52 Hz, 1H), 7.57 (d, J=7.64 Hz, 1H), 7.43-7.40 (m, 2H), 7.35-7.31 (m, 2H), 7.16 (dd, J=1.72, 5.52 Hz, 1H), 7.07 (d, J=1.6 Hz, 1H), 6.08 (dd, J=2.68, 7.64 Hz, 1H), 5.95 (d, J=2.68 Hz, 1H), 4.62-4.61 (m, 2H), 4.38-4.35 (m, 2H). ES-MS [M+1]$^+$: 361.3.

The following compounds were prepared in an analogous manner by first preparing the appropriate synthetic intermediate by use of the synthetic procedures indicated next to each compound:

| No. | Name | Example used to prepare intermediate compound | ES-MS [M + 1]$^+$ |
|---|---|---|---|
| 50 | 1-(4-fluorophenyl)-4-(2-(pyridin-2-yloxy)ethoxy)pyridin-2(1H)-one | 1, 7 | 327.3 |
| 51 | 1-(4-fluorophenyl)-4-(2-((3-fluoropyridin-2-yl)oxy)ethoxy)pyridin-2(1H)-one | 1, 7 | 345.3 |
| 52 | 1-(4-fluorophenyl)-4-(2-((5-fluoropyridin-2-yl)oxy)ethoxy)pyridin-2(1H)-one | 1, 7 | 345.2 |
| 53 | 4-(2-((6-chloropyridin-2-yl)oxy)ethoxy)-1-(4-fluorophenyl)pyridin-2(1H)-one | 1, 7 | 361.3 |
| 54 | 4-(2-((3-chloropyridin-2-yl)oxy)ethoxy)-1-(4-fluorophenyl)pyridin-2(1H)-one | 1, 7 | 361.2 |
| 55 | 4-(2-((5-chloropyridin-2-yl)oxy)ethoxy)-1-(4-fluorophenyl)pyridin-2(1H)-one | 1, 7 | 361.2 |
| 56 | 2-(2-((1-(4-fluorophenyl)-2-oxo-1,2-dihydropyridin-4-yl)oxy)ethoxy)nicotinonitrile | 1, 7 | 352.2 |
| 57 | 2-(2-((1-(4-fluorophenyl)-2-oxo-1,2-dihydropyridin-4-yl)oxy)ethoxy)isonicotinonitrile | 1, 7 | 352.2 |
| 58 | 6-(2-((1-(4-fluorophenyl)-2-oxo-1,2-dihydropyridin-4-yl)oxy)ethoxy)nicotinonitrile | 1, 7 | 352.3 |
| 59 | 6-(2-((1-(4-fluorophenyl)-2-oxo-1,2-dihydropyridin-4-yl)oxy)ethoxy)picolinonitrile | 1, 7 | 352.2 |

Example 19. Biological Activity

A. mGlu$_3$ Ca$^{2+}$ Flux Assay

G$_{\alpha 15}$/TREx cells stably expressing rat mGlu$_3$ were plated in black-walled, clear-bottomed, poly-D-lysine coated 384-well plates in 20 µL of assay medium (DMEM containing 10% dialyzed FBS, 20 mM HEPES, 25 ng/mL tetracycline, 100 units/mL penicillin/streptomycin plus 250 ng/mL Fungizone, and 1 mM sodium pyruvate) at a density of 15K cells/well. The cells were grown overnight at 37° C. in the presence of 5% CO$_2$. The next day, medium was removed and the cells incubated with 20 µL of 2.3 LM Fluo-4, AM prepared as a 2.3 mM stock in DMSO and mixed in a 1:1 ratio with 10% (w/v) pluronic acid F-127 and diluted in assay buffer (Hank's balanced salt solution, 20 mM HEPES, and 2.5 mM probenecid) for 60 minutes at room temperature. Dye was removed, 20 µL of assay buffer was added, and the plate was incubated for 10 minutes at room temperature.

Ca$^{2+}$ flux was measured using the Functional Drug Screening System (FDSS7000, Hamamatsu, Japan). After establishment of a fluorescence baseline for about 3 seconds, the compounds of the present invention were added to the cells, and the response in cells was measured. 2.3 minutes later an EC$_{20}$ concentration of the mGlu$_3$ receptor agonist glutamate was added to the cells, and the response of the cells was measured for 1.9 minutes; an EC$_{80}$ concentration of agonist was added and readings taken for an additional 1.7 minutes. All test compounds were dissolved and diluted to a concentration of 10 mM in 100% DMSO. Compounds were then serially diluted 1:3 in DMSO into 10 point concentration response curves, transferred to daughter plates, and further diluted into assay buffer to a 2× stock. Calcium fluorescence measures were recorded as fold over basal fluorescence; raw data was then normalized to the maximal response to glutamate. Antagonism of the agonist response of the mGlu$_3$ receptor in the present invention was observed as a decrease in response to nearly maximal concentrations of glutamate in the presence of compound compared to the response to glutamate in the absence of compound.

The raw data file containing all time points was used as the data source in the analysis template. This was saved by the FDSS as a tab-delimited text file. Data were normalized using a static ratio function (F/F$_0$) for each measurement of the total 360 values per well divided by each well's initial value. Data were then reduced to peak amplitudes (Max−Initial Min) using a time range that starts approximately 3 seconds prior to the glutamate EC$_{80}$ addition and continues for approximately 90 seconds. This is sufficient time to capture the peak amplitude of the cellular calcium response. Individual amplitudes were expressed as % E$_{Max}$ by multiplying each amplitude by 100 and then dividing the product by the mean of the amplitudes derived from the glutamate EC$_{Max}$-treated wells. EC$_{50}$ values for test compounds were generated by fitting the normalized values versus the log of the test compound concentration (in mol/L) using a 4 parameter logistic equation where none of the parameters were fixed. Each of the three values collected at each concentration of test compound were weighted evenly.

A compound was designated as a negative allosteric modulator (NAM) if the compound showed a concentration-dependent decrease in the glutamate EC$_{80}$ addition. For NAMs, potency (IC$_{50}$) and maximum response (% Glu Max), i.e. the amplitude of response in the presence of 30

µM test compound as a percentage of the maximal response to glutamate, are reported. For NAMs that show a decrease in the $EC_{80}$ response, but do not hit a plateau, the average of the maximum response at a single concentration (30 µM) was determined (% Glu Max) and potencies were reported as ">10,000 nM". Compounds with no measurable activity are designated as ">30,000 nM" since the top concentration of compound tested in the assay is 30 µM.

B. $mGlu_2$ $Ca^{2+}$ Flux Assay $G_{\alpha15}$ HEK293 cells stably expressing rat $mGlu_2$ were plated in black-walled, clear-bottomed, poly-D-lysine coated 384-well plates in 20 µL of assay medium (DMEM containing 10% dialyzed FBS, 20 mM HEPES, and 1 mM sodium pyruvate) at a density of 12K cells/well. The cells were grown overnight at 37° C. in the presence of 5% $CO_2$. The next day, medium was removed and the cells incubated with 20 µL of 2.3 LM Fluo-4, AM prepared as a 2.3 mM stock in DMSO and mixed in a 1:1 ratio with 10% (w/v) pluronic acid F-127 and diluted in assay buffer (Hank's balanced salt solution, 20 mM HEPES, and 2.5 mM probenecid) for 45 minutes at 37° C. Dye was removed, 20 µL of assay buffer was added, and the plate was incubated for 5 minutes at room temperature.

$Ca^{2+}$ flux was measured using the Functional Drug Screening System (FDSS7000, Hamamatsu, Japan). After establishment of a fluorescence baseline for about 3 seconds, the compounds of the present invention were added to the cells, and the response in cells was measured. 2.3 minutes later an $EC_{20}$ concentration of the $mGlu_2$ receptor agonist glutamate was added to the cells, and the response of the cells was measured for 1.9 minutes; an $EC_{80}$ concentration of agonist was added and readings taken for an additional 1.7 minutes. All test compounds were dissolved and diluted to a concentration of 10 mM in 100% DMSO. Compounds were then serially diluted 1:3 in DMSO into 10 point concentration response curves, transferred to daughter plates, and further diluted into assay buffer to a 2× stock. Calcium fluorescence measures were recorded as fold over basal fluorescence; raw data was then normalized to the maximal response to glutamate. Antagonism of the agonist response of the $mGlu_2$ receptor in the present invention was observed as a decrease in response to nearly maximal concentrations of glutamate in the presence of compound compared to the response to glutamate in the absence of compound.

The raw data file containing all time points was used as the data source in the analysis template. This was saved by the FDSS as a tab-delimited text file. Data were normalized using a static ratio function ($F/F_0$) for each measurement of the total 360 values per well divided by each well's initial value. Data were then reduced to peak amplitudes (Max-Initial Min) using a time range that starts approximately 3 seconds prior to the glutamate $EC_{80}$ addition and continues for approximately 90 seconds. This is sufficient time to capture the peak amplitude of the cellular calcium response. Individual amplitudes were expressed as % $EC_{Max}$ by multiplying each amplitude by 100 and then dividing the product by the mean of the amplitudes derived from the glutamate $EC_{Max}$-treated wells. $IC_{50}$ values for test compounds were generated by fitting the normalized values versus the log of the test compound concentration (in mol/L) using a 4 parameter logistic equation where none of the parameters were fixed. Each of the three values collected at each concentration of test compound were weighted evenly.

A compound was designated as a negative allosteric modulator (NAM) if the compound showed a concentration-dependent decrease in the glutamate $EC_{80}$ addition. For NAMs, potency ($IC_{50}$) and maximum response (% Glu Max), i.e. the amplitude of response in the presence of 30 µM test compound as a percentage of the maximal response to glutamate, are reported. For NAMs that show a decrease in the $EC_{80}$ response, but do not hit a plateau, the average of the maximum response at a single concentration (30 µM) was determined (% Glu Max) and potencies were reported as ">10,000 nM". Compounds with no measurable activity are designated as ">30,000 nM" since the top concentration of compound tested in the assay is 30 µM.

C. $mGlu_5$ $Ca^{2+}$ Flux Assay

HEK 293A cells stably expressing rat $mGlu_5$ were plated in black-walled, clear-bottomed, poly-D-lysine coated 384-well plates in 20 µL of assay medium (DMEM containing 10% dialyzed FBS, 20 mM HEPES, 100 units/mL penicillin/streptomycin plus 250 ng/mL Fungizone, and 1 mM sodium pyruvate) at a density of 20K cells/well. The cells were grown overnight at 37° C. in the presence of 5% $CO_2$. The next day, medium was removed and the cells incubated with 20 µL of 2.3 LM Fluo-4, AM prepared as a 2.3 mM stock in DMSO and mixed in a 1:1 ratio with 10% (w/v) pluronic acid F-127 and diluted in assay buffer (Hank's balanced salt solution, 20 mM HEPES, and 2.5 mM probenecid) for 45 minutes at 37° C. Dye was removed, 20 µL of assay buffer was added, and the plate was incubated for 5 minutes at room temperature.

$Ca^{2+}$ flux was measured using the Functional Drug Screening System (FDSS7000, Hamamatsu, Japan). After establishment of a fluorescence baseline for about 3 seconds, the compounds of the present invention were added to the cells, and the response in cells was measured. 2.3 minutes later an $EC_{20}$ concentration of the $mGlu_5$ receptor agonist glutamate was added to the cells, and the response of the cells was measured for 1.9 minutes; an $EC_{80}$ concentration of agonist was added and readings taken for an additional 1.7 minutes. All test compounds were dissolved and diluted to a concentration of 10 mM in 100% DMSO. Compounds were then serially diluted 1:3 in DMSO into 10 point concentration response curves, transferred to daughter plates, and further diluted into assay buffer to a 2× stock. Calcium fluorescence measures were recorded as fold over basal fluorescence; raw data was then normalized to the maximal response to glutamate. Potentiation of the agonist response of the $mGlu_5$ receptor in the present invention was observed as an increase in response to submaximal concentrations of glutamate in the presence of compound compared to the response to glutamate in the absence of compound. Antagonism of the agonist response of the $mGlu_5$ receptor in the present invention was observed as a decrease in response to nearly maximal concentrations of glutamate in the presence of compound compared to the response to glutamate in the absence of compound.

The raw data file containing all time points was used as the data source in the analysis template. This was saved by the FDSS as a tab-delimited text file. Data were normalized using a static ratio function ($F/F_0$) for each measurement of the total 360 values per well divided by each well's initial value. Data were then reduced to peak amplitudes (Max-Initial Min) using a time range that starts approximately 3 seconds prior to the glutamate $EC_{20}/EC_{80}$ addition and continues for approximately 90-120 seconds. This is sufficient time to capture the peak amplitude of the cellular calcium response. Individual amplitudes were expressed as % $E_{Max}$ by multiplying each amplitude by 100 and then dividing the product by the mean of the amplitudes derived from the glutamate $EC_{Max}$-treated wells. $EC_{50}$ values for test compounds were generated by fitting the normalized values versus the log of the test compound concentration (in mol/L) using a 4 parameter logistic equation where none of the parameters were fixed. Each of the three values collected at each concentration of test compound were weighted evenly.

A compound was designated as a positive allosteric modulator (PAM) if the compound showed a concentration-dependent increase in the glutamate $EC_{20}$ addition. For PAMs, potency ($EC_{50}$) and maximum response (% Glu Max), i.e. the amplitude of response in the presence of 30 µM test compound as a percentage of the maximal response to glutamate, are reported. For PAMs that show an increase in the $EC_{20}$ response, but do not hit a plateau, the average of the maximum response at a single concentration (30 µM) was determined (% Glu Max) and potencies were reported as ">10,000 nM". A compound was designated as a negative allosteric modulator (NAM) if the compound showed a concentration-dependent decrease in the glutamate $EC_{80}$ addition. For NAMs, potency ($IC_{50}$) and maximum response (% Glu Max), i.e. the amplitude of response in the presence of 30 µM test compound as a percentage of the maximal response to glutamate, are reported. For NAMs that show a decrease in the $EC_{80}$ response, but do not hit a plateau, the average of the maximum response at a single concentration (30 µM) was determined (% Glu Max) and potencies were reported as ">10,000 nM". Compounds with no measurable activity are designated as ">30,000 nM" since the top concentration of compound tested in the assay is 30 µM.

B. Results and Discussion of Biological Activity Data

The results of these assays are shown in Table 1. The data in Table 1 demonstrates that the disclosed compounds are negative allosteric modulators of $mGlu_2$ and show high affinity for the $mGlu_2$ receptor(s). Data is from a single experiment unless otherwise noted. Data that is an average of two experiments is noted as "n=2" while data that is an average of three or more experiments is presented as the average plus or minus the standard error of the mean. Compounds with measurable activity at $mGlu_5$ are positive allosteric modulators (PAMs) of that receptor unless otherwise noted as negative allosteric modulators (NAM).

TABLE 1

| Compound | rat $mGlu_3$ $IC_{50}$ (nM) | rat $mGlu_3$ Glu max (%) | rat $mGlu_2$ $IC_{50}$ (nM) | rat $mGlu_2$ Glu max (%) | rat $mGlu_5$ $EC_{50}$ or $IC_{50}$ (nM) | rat $mGlu_5$ Glu max (%) |
|---|---|---|---|---|---|---|
| W | 13,000 | 14.52 | — | — | — | — |
| 1 | 728 | 0.69 | >30,000 | N/A | >30,000 | N/A |
| 2 | 5410 | 1.95 | >30,000 | N/A | — | — |
| 3 | 3890 | 1.42 | >30,000 | N/A | — | — |
| 4 | 4000 | 0.00 | >30,000 | N/A | — | — |
| 5 | 1160 | 1.60 | >30,000 | N/A | >10,000 | 42.45 |
| 6 | >30,000 | N/A | — | — | — | — |
| 7 | >10,000 | 15.48 | — | — | — | — |
| 8 | >30,000 | N/A | — | — | — | — |
| 9 | >30,000 | N/A | — | — | — | — |
| 10 | 3930 | 1.16 | >30,000 | N/A | — | — |
| 11 | >30,000 | N/A | >30,000 | N/A | — | — |
| 12 | >10,000 | 33.16 | >30,000 | N/A | — | — |
| 13 | >30,000 | N/A | >30,000 | N/A | — | — |
| 14 | 296 | 1.61 | >30,000 | N/A | 3540 | 77.45 |
| 15 | 219 | 2.44 | >30,000 | N/A | 427 | 82.99 |
| 16 | >10,000 | 23.95 | >30,000 | N/A | — | — |
| 17 | 211 | 1.84 | >30,000 | N/A | 1190 | 96.85 |
| 18 | 725 ± 227 | 1.45 ± 0.14 | >30,000 | N/A | 567 | 97.30 |
| 19 | 434 | 2.01 | >30,000 | N/A | 1970 | 88.03 |
| 20 | 323 | 1.63 | >30,000 | N/A | 344 | 91.05 |
| 21 | 799 | 7.25 | >30,000 | N/A | 818 | 28.27 |
| 22 | 559 | 1.16 | >30,000 | N/A | 6020 | 87.02 |
| 23 | 522 | 3.44 | >30,000 | N/A | 1310 | 26.84 |
| 24 | 3170 | 0.49 | >30,000 | N/A | — | — |
| 25 | 6750 | −2.95 | >30,000 | N/A | — | — |
| 26 | 3410 | −5.24 | >30,000 | N/A | — | — |
| 27 | 1870 | 4.56 | >30,000 | N/A | — | — |
| 28 | 1270 | 10.11 | >30,000 | N/A | 1220 | 89.77 |
| 29 | 3870 | 5.86 | >30,000 | N/A | — | — |
| 30 | 897 | 2.48 | >30,000 | N/A | 1870 | 92.79 |
| 31 | 514 | 1.95 | >30,000 | N/A | 1460 | 93.15 |
| 32 | 1050 | −0.56 | >30,000 | N/A | 1500 | 94.12 |
| 33 | 917 | −0.23 | >30,000 | N/A | 6850 | 94.13 |
| 34 | 1450 | 1.32 | >30,000 | N/A | — | — |
| 35 | 1460 | 2.27 | >30,000 | N/A | — | — |
| 36 | 3180 | −1.16 | >30,000 | N/A | — | — |
| 37 | 1840 | 2.05 | >30,000 | N/A | — | — |
| 38 | 980 | 0.85 | >30,000 | N/A | — | — |
| 39 | 634 | 1.56 | >30,000 | N/A | 10,000 | 81.08 |
| 40 | 4740 | −4.22 | >30,000 | N/A | — | — |
| 41 | 715 | 0.13 | >30,000 | N/A | >10,000 (weak NAM) | 29.14 |
| 42 | 1130 | 0.74 | >30,000 | N/A | — | — |
| 43 | >10,000 | 37.34 | >30,000 | N/A | — | — |
| 44 | 10,000 | 1.83 | >30,000 | N/A | — | — |
| 45 | 701 | 0.88 | >30,000 | N/A | >10,000 | 35.46 |
| 46 | 2790 | 0.41 | >30,000 | N/A | — | — |

TABLE 1-continued

| Compound | rat mGlu$_3$ IC$_{50}$ (nM) | rat mGlu$_3$ Glu max (%) | rat mGlu$_2$ IC$_{50}$ (nM) | rat mGlu$_2$ Glu max (%) | rat mGlu$_5$ EC$_{50}$ or IC$_{50}$ (nM) | rat mGlu$_5$ Glu max (%) |
|---|---|---|---|---|---|---|
| 47 | >10,000 | 36.68 | >30,000 | N/A | — | — |
| 48 | 5560 | −2.79 | >30,000 | N/A | — | — |
| 49 | 563 | 0.73 | >30,000 | N/A | 8800 | 82.32 |
| 50 | 1940 | −0.52 | >30,000 | N/A | — | — |
| 51 | 1280 | 0.20 | >30,000 | N/A | — | — |
| 52 | 1060 | 0.26 | >30,000 | N/A | — | — |
| 53 | 4270 | −1.66 | >30,000 | N/A | — | — |
| 54 | 443 | 0.96 | >30,000 | N/A | 7820 | 94.01 |
| 55 | 729 | 0.32 | >30,000 | N/A | >10,000 | 25.23 |
| 56 | >10,000 | 18.04 | >30,000 | N/A | — | — |
| 57 | 753 | −0.40 | >30,000 | N/A | >10,000 | 38.68 |
| 58 | 1380 | 1.06 | >30,000 | N/A | — | — |
| 59 | >10,000 | 35.85 | >30,000 | N/A | — | — |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound of formula (I)

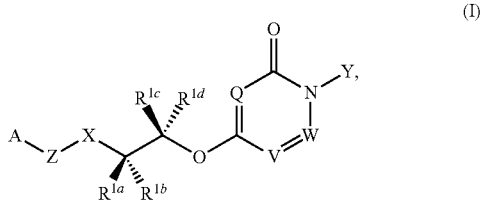

(I)

or a pharmaceutically acceptable salt thereof, wherein

A is phenyl, or pyridyl, wherein A is substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and OR$^4$; wherein R$^4$ is hydrogen, $C_1$-$C_3$ alkyl, or $C_1$-$C_3$ fluoroalkyl;

Z is a bond;

X is —(CR$^{1e}$R$^{1f}$)$_m$—, O, S, or NR$^2$;

R$^{1e}$ and R$^{1f}$ are each independently hydrogen;

m is 1;

R$^2$ is hydrogen, $C_1$-$C_3$ alkyl or $C_1$-$C_3$ haloalkyl;

R$^{1a}$, R$^{1b}$, R$^{1c}$, and R$^{1d}$ are each independently hydrogen, fluoro $C_1$-$C_3$ alkyl or $C_1$-$C_3$ haloalkyl;

Q is N or CR$^{3a}$;

V is N or CR$^{3b}$;

W is CR$^{3c}$; wherein no more than one of Q and V is N;

R$^{3a}$, R$^{3b}$, and R$^{3c}$ are hydrogen; and

Y is phenyl or monocyclic heteroaryl, wherein Y is substituted with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_6$ cycloalkyl, $C_3$-$C_8$ fluorocycloalkyl, OR$^4$, and NR$^{5a}$R$^{5b}$; wherein R$^4$ is hydrogen, $C_1$-$C_6$ alkyl or $C_1$-$C_6$ fluoroalkyl; and R$^{5a}$ and R$^{5b}$ are each independently hydrogen, $C_1$-$C_6$ alkyl, $C_3$-$C_8$ cycloalkyl, or $C_1$-$C_6$ heteroalkyl; or R$^{5a}$ and R$^{5b}$ together with the nitrogen atom to which they are attach form a heterocycle; wherein each R$^{5a}$ and R$^{5b}$ are substituted with 0-3 fluorine atoms.

2. The compound of claim 1, or a pharmaceutically acceptable salt thereof, wherein X is O, S, or NR$^2$; wherein R$^2$ is hydrogen, $C_1$-$C_3$ alkyl or $C_1$-$C_3$ fluoroalkyl.

3. The compound of claim 1, or a pharmaceutically acceptable salt thereof, wherein R$^{1a}$, R$^{1b}$, R$^{1c}$ and R$^{1d}$ are each independently hydrogen or $C_1$-$C_3$ alkyl.

4. The compound of claim 1, or a pharmaceutically acceptable salt thereof, wherein Q is CR$^{3a}$; V is CR$^{3b}$; and W is CR$^{3c}$.

5. The compound of claim 1, or a pharmaceutically acceptable salt thereof, wherein Q is N; V is CR$^{3b}$; and W is CR$^{3c}$.

6. The compound of claim 1, or a pharmaceutically acceptable salt thereof, wherein Y is phenyl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$) alkyl, and OR$^4$; wherein R$^4$ is hydrogen, $C_1$-$C_3$ alkyl, or $C_1$-$C_3$ fluoroalkyl.

7. The compound of claim 1, or a pharmaceutically acceptable salt thereof, wherein Y is a monocyclic heteroaryl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and OR$^4$; wherein R$^4$ is hydrogen, $C_1$-$C_3$ alkyl, or $C_1$-$C_3$ fluoroalkyl.

8. The compound of claim 1, or a pharmaceutically acceptable salt thereof, wherein A is phenyl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and OR$^4$; wherein R$^4$ is hydrogen, $C_1$-$C_3$ alkyl, or $C_1$-$C_3$ fluoroalkyl;

X is O;

R$^{1a}$, R$^{1b}$, R$^{1c}$ and R$^{1d}$ are each independently hydrogen or $C_1$-$C_3$ alkyl;

Q is N or CR$^{3a}$;

V is CR$^{3b}$;

W is CR$^{3c}$;

R$^{3a}$, R$^{3b}$ and R$^{3c}$ are hydrogen; and

Y is phenyl substituted with 0-3 substituents independently selected from fluoro, chloro, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl.

9. The compound of claim 1, or a pharmaceutically acceptable salt thereof, wherein A is substituted with 0-2 substituents independently selected from fluoro, chloro, methoxyethyl, and cyano.

10. The compound of claim 1, selected from the group consisting of:
1-(4-fluorophenyl)-4-(3-phenylpropoxy)pyridin-2(1H)-one;
1-(4-fluorophenyl)-4-(2-phenoxyethoxy)pyridin-2(1H)-one;
1-(4-fluorophenyl)-4-(2-(phenylthio)ethoxy)pyridin-2(1H)-one;
1-(4-fluorophenyl)-4-(2-(methyl(phenyl)amino)ethoxy)pyridin-2(1H)-one;
1-(3-fluorophenyl)-4-(2-phenoxyethoxy)pyridin-2(1H)-one;
1-(2-fluorophenyl)-4-(2-phenoxyethoxy)pyridin-2(1H)-one;
1-(3,4-difluorophenyl)-4-(2-phenoxyethoxy)pyridin-2(1H)-one;
1-(3,5-difluorophenyl)-4-(2-phenoxyethoxy)pyridin-2(1H)-one;
3-(2-oxo-4-(2-phenoxyethoxy)pyridin-1(2H)-yl)benzonitrile;
3-fluoro-5-(2-oxo-4-(2-phenoxyethoxy)pyridin-1(2H)-yl)benzonitrile;
4-(2-oxo-4-(2-phenoxyethoxy)pyridin-1(2H)-yl)benzonitrile;
4-(2-phenoxyethoxy)-2H-[1,2'-bipyridin]-2-one;
6'-fluoro-4-(2-phenoxyethoxy)-2H-[1,2'-bipyridin]-2-one;
6'-fluoro-4-(2-phenoxyethoxy)-2H-[1,3'-bipyridin]-2-one;
4-(2-phenoxyethoxy)-2H-[1,4'-bipyridin]-2-one;
4-(2-(2-fluorophenoxy)ethoxy)-1-(4-fluorophenyl)pyridin-2(1H)-one;
4-(2-(3-fluorophenoxy)ethoxy)-1-(4-fluorophenyl)pyridin-2(1H)-one;
4-(2-(4-fluorophenoxy)ethoxy)-1-(4-fluorophenyl)pyridin-2(1H)-one;
4-(2-(2,3-difluorophenoxy)ethoxy)-1-(4-fluorophenyl)pyridin-2(1H)-one;
4-(2-(2,4-difluorophenoxy)ethoxy)-1-(4-fluorophenyl)pyridin-2(1H)-one;
4-(2-(2,5-difluorophenoxy)ethoxy)-1-(4-fluorophenyl)pyridin-2(1H)-one;
4-(2-(2,6-difluorophenoxy)ethoxy)-1-(4-fluorophenyl)pyridin-2(1H)-one;
4-(2-(2-chlorophenoxy)ethoxy)-1-(4-fluorophenyl)pyridin-2(1H)-one;
4-(2-(3-chlorophenoxy)ethoxy)-1-(4-fluorophenyl)pyridin-2(1H)-one;
4-(2-(4-chlorophenoxy)ethoxy)-1-(4-fluorophenyl)pyridin-2(1H)-one;
1-(4-fluorophenyl)-4-(2-((2-fluoropyridin-3-yl)oxy)ethoxy)pyridin-2(1H)-one;
3-(2-((1-(4-fluorophenyl)-2-oxo-1,2-dihydropyridin-4-yl)oxy)ethoxy)benzonitrile;
4-(2-((1-(4-fluorophenyl)-2-oxo-1,2-dihydropyridin-4-yl)oxy)ethoxy)benzonitrile;
1-(4-fluorophenyl)-4-(2-(4-(methoxymethyl)phenoxy)ethoxy)pyridin-2(1H)-one;
1-(4-fluorophenyl)-4-(2-(pyridin-3-yloxy)ethoxy)pyridin-2(1H)-one;
1-(4-fluorophenyl)-4-(2-(6-fluoropyridin-3-yl)oxy)ethoxy)pyridin-2(1H)-one;
4-(2((5-chloropyridin-3-yl)oxy)ethoxy)-1-(4-fluorophenyl)pyridin-2(1H)-one;
4-(2-((4-chloropyridin-3-yl)oxy)ethoxy)-1-(4-fluorophenyl)pyridin-2(1H)-one;
4-(2-((2-chloropyridin-3-yl)oxy)ethoxy)-1-(4-fluorophenyl)pyridin-2(1H)-one;
1-(4-fluorophenyl)-4-(2-(pyridin-2-yloxy)ethoxy)pyridin-2(1H)-one;
1-(4-fluorophenyl)-4-(2-((3-fluoropyridin-2-yl)oxy)ethoxy)pyridin-2(1H)-one;
1-(4-fluorophenyl)-4-(2-((5-fluoropyridin-2-yl)oxy)ethoxy)pyridin-2(1H)-one;
4-(2-((6-chloropyridin-2-yl)oxy)ethoxy)-1-(4-fluorophenyl)pyridin-2(1H)-one;
4-(2-((3-chloropyridin-2-yl)oxy)ethoxy)-1-(4-fluorophenyl)pyridin-2(1H)-one;
4-(2-((4-chloropyridin-2-yl)oxy)ethoxy)-1-(4-fluorophenyl)pyridin-2(1H)-one;
4-(2-((5-chloropyridin-2-yl)oxy)ethoxy)-1-(4-fluorophenyl)pyridin-2(1H)-one;
2-(2-((1-(4-fluorophenyl)-2-oxo-1,2-dihydropyridin-4-yl)oxy)ethoxy)nicotinonitrile;
2-(2-((1-(4-fluorophenyl)-2-oxo-1,2-dihydropyridin-4-yl)oxy)ethoxy)isonicotinonitrile;
6-(2-((1-(4-fluorophenyl)-2-oxo-1,2-dihydropyridin-4-yl)oxy)ethoxy)nicotinonitrile;
6-(2-((1-(4-fluorophenyl)-2-oxo-1,2-dihydropyridin-4-yl)oxy)ethoxy)picolinonitrile;
1-(4-fluorophenyl)-4-(2-phenoxyethoxy)pyrimidin-2(1H)-one;
1-(3-fluorophenyl)-4-(2-phenoxyethoxy)pyrimidin-2(1H)-one;
1-(3,4-difluorophenyl)-4-(2-phenoxyethoxy)pyrimidin-2(1H)-one;
1-(5-fluoropyridin-2-yl)-4-(2-phenoxyethoxy)pyrimidin-2(1H)-one;
3-(4-fluorophenyl)-6-(2-phenoxyethoxy)pyrimidin-4(3H)-one;
2-oxo-4-(2-phenoxyethoxy)-2H-[1,3'-bipyridine]-5'-carbonitrile;
5'-fluoro-4-(2-phenoxyethoxy)-2H-[1,3'-bipyridin]-2-one;
1-(4-fluorophenyl)-4-(2-phenoxypropoxy)pyridin-2(1H)-one;
1-(4-fluorophenyl)-4-((1-phenoxypropan-2-yl)oxy)pyridin-2(1H)-one; and
4-(2-(Benzyloxy)ethoxy)-1-(4-fluorophenyl)pyridin-2(1H)-one;
or a pharmaceutically acceptable salt thereof.

11. A pharmaceutical composition comprising a therapeutically effective amount of the compound of claim 1, or a pharmaceutically acceptable salt thereof, in combination with one or more pharmaceutically acceptable carriers.

* * * * *

UNITED STATES PATENT AND TRADEMARK OFFICE
CERTIFICATE OF CORRECTION

PATENT NO. : 10,399,948 B2
APPLICATION NO. : 15/549944
DATED : September 3, 2019
INVENTOR(S) : P. Jeffrey Conn et al.

Page 1 of 1

It is certified that error appears in the above-identified patent and that said Letters Patent is hereby corrected as shown below:

In the Specification

Replace the following paragraph:

"This invention was made with government support under Grant number 1 R01 MH99269-01 awarded by the National Institute of Mental Health (NIMH). The government has certain rights in the invention."

With the paragraph:

--This invention was made with government support under grant number MH099269 awarded by the National Institutes of Health. The government has certain rights in the invention.--

Signed and Sealed this
Nineteenth Day of May, 2020

Andrei Iancu
*Director of the United States Patent and Trademark Office*